US008623854B2

(12) United States Patent
Sullivan et al.

(10) Patent No.: US 8,623,854 B2
(45) Date of Patent: Jan. 7, 2014

(54) NUCLEAR EXPORT INHIBITORS OF TOPOISOMERASE II ALPHA

(75) Inventors: Daniel M. Sullivan, Tampa, FL (US); Joel G. Turner, Tampa, FL (US); Thomas C. Rowe, Gainesville, FL (US); David A. Ostrov, Gainesville, FL (US)

(73) Assignees: H. Lee Moffitt Cancer Center and Research Institute, Inc., Tampa, FL (US); University of Florida Research Foundation, Inc., Gainesville, FL (US)

( * ) Notice: Subject to any disclaimer, the term of this patent is extended or adjusted under 35 U.S.C. 154(b) by 47 days.

(21) Appl. No.: 13/159,016

(22) Filed: Jun. 13, 2011

(65) Prior Publication Data
US 2011/0275581 A1 Nov. 10, 2011

Related U.S. Application Data

(63) Continuation of application No. PCT/US2009/067922, filed on Dec. 14, 2009.

(60) Provisional application No. 61/122,098, filed on Dec. 12, 2008.

(51) Int. Cl.
*A01N 43/00* (2006.01)
*A61K 31/33* (2006.01)
*A01N 57/00* (2006.01)
*A61K 31/66* (2006.01)
*A01N 43/66* (2006.01)
*A61K 31/53* (2006.01)
*A01N 43/50* (2006.01)
*A61K 31/415* (2006.01)

(52) U.S. Cl.
USPC ........... 514/183; 514/124; 514/244; 514/245; 514/401

(58) Field of Classification Search
USPC .......................... 514/183, 124, 244, 245, 401
See application file for complete search history.

(56) References Cited

FOREIGN PATENT DOCUMENTS

WO WO 2009153589 A1 * 12/2009

OTHER PUBLICATIONS

Golubovskaya et al. J. of Med. Chemistry, published online Nov. 2008, vol. 51, Issue 23, pp. 7405-7416.*
Myeloma Beacon, Doxorubicin, Oct. 2008, pp. 1-3.*
Menendez et al., Nuclear Export Inhibitor Leptomycin B Induces the Appearance of Novel Forms of Human Mdm2 Protein, British Journal of Cancer, 2003, vol. 88, pp. 636-643.
Turner et al., Human Topoisomerase IIalpha Nuclear Export is Mediated by Two CRM-1-Dependent Nuclear Export Signals, Journal of Cell Science, 2004, vol. 117, pp. 3061-3071.
Jang et al., Leptomycin B, an Inhibitor of the Nuclear Export Receptor CRM1, Inhibits COX-2 Expression, The Journal of Biological Chemistry, 2003, vol. 278, No. 5, pp. 2773-2776.
International Search Report for International application No. PCT/US2009/067922 dated Jun. 23, 2011.
Nakamura et al., Forkhead Transcription Factors Are Critical Effectors of Cell Death and Cell Cycle Arrest Downstream of PTEN, Molecular and Cellular Biology, 2000, vol. 20, No. 23, pp. 8969-8982.
Min et al., Cytoplasmic Mislocalization of p27Kip1 Protein Is Associated with Constitutive Phosphorylation of Akt or Protein Kinase B and Poor Prognosis in Acute Myelogenous Leukemia, Cancer Research, 2004, vol. 64, pp. 5225-5231.
Oloumi et al., Changes in Subcellular Distribution of Topoisomerase IIalpha Correlate with Etoposide Resistance in Multicell Spheroids and Xenograft Tumors, Cancer Research, 2000, vol. 60, pp. 5747-5753.
Hazlehurst et al., Cell Adhesion to Fibronectin (CAM-DR) Influences Acquired Mitoxantrone Resistance in U937 Cells, Cancer Research, 2006, vol. 66, No. 4, pp. 2338-2345.
Hazlehurst et al., Reduction in Drug-Induced DNA Double-Strand Breaks Associated with Beta1 Integrin-Mediated Adhesion Correlates with Drug Resistance in U937 Cells, Blood, 2001, vol. 98, pp. 1897-1903.
Chen et al., The FA/BRCA Pathway is Involved in Melphalan-Induced DNA Interstrand Cross-Link Repair and Accounts for Melphalan Resistance in Multiple Myeloma Cells, Blood, 2005, vol. 106, pp. 698-705.
Falini et al., Both Carboxy-Terminus NES Motif and Mutated Tryptophan(s) are Crucial for Aberrant Nuclear Export of Nucleophosmin Leukemic Mutants in NPMc+ AML, Blood, 2006, vol. 107, pp. 4514-4523.
Geyer et al., The MDM2 RING-finger Domain is Required to Promote p53 Nuclear Export, Nature Cell Biology, 2000, vol. 2, No. 9, pp. 569-573.
Newlands et al., Phase I Trial of Elactocin, British Journal of Cancer, 1996, vol. 74, pp. 648-649.
Rasheed et al., Mechanisms of Resistance to Topoisomerase I-Targeting Drugs, Oncogene, 2003, vol. 22, pp. 7296-7304.
Sullivan et al., Purification and Characterization of an Altered Topoisomerase II from a Drug-Resistant Chinese Hamster Ovary Cell Line, Biochemistry, 1989, vol. 28, pp. 5680-5687.
Takenaka et al., Nuclear Export of Phosphorylated Galectin-3 Regulates Its Antipoptotic Activity in Response to Chemotherapeutic Drugs, Molecular and Cellular Biology, 2004, vol. 24, No. 10, pp. 4395-4406.

(Continued)

Primary Examiner — Samira Jean-Louis
(74) Attorney, Agent, or Firm — Michele L. Lawson; Michael M. McGaw; Smith & Hopen, P.A.

(57) ABSTRACT

A method of treating cancer in a subject comprising the step of administering to the subject in need thereof an effective amount of a combination of a compound that binds a nuclear export signal (NES inhibitor) on topoisomerase IIα and a topoisomerase inhibitor. Twenty small molecule inhibitors (SMI) that bind to the two nuclear export sequences (NES) topo IIα have been identified from the NCI database using computer-generated molecular modeling. These SMI will improve the effectiveness of topo II directed therapeutics, particularly in the treatment of diseases such as multiple myeloma (MM). In vitro apoptosis assays indicate that these drugs may be effective as single agents or in combination with currently used cancer drugs that target topo II.

8 Claims, 8 Drawing Sheets

(56) References Cited

OTHER PUBLICATIONS

Valkov et al., Cell Density-Dependent VP-16 Sensitivity of Leukaemic Cells is Accompanied by the Translocation of Topoisomerase IIalpha from the Nucleus to the Cytoplasm, British Journal of Haematology, 2000, vol. 108, pp. 331-345.

Xiao et al., The Topoisomerase IIbeta Circular Clamp Arrests Transcription and Signals a 26S Proteasome Pathway, PNAS, 2003, vol. 100, No. 6, pp. 3239-3244.

Davis et al., Controlling Protein Compartmentalization to Overcome Disease, Pharmaceutical Research, 2007, vol. 24, No. 1, pp. 17-27.

Engel et al., The Cytoplasmic Trafficking of DNA Topoisomerase IIalpha Correlates with Etoposide Resistance in Human Myeloma Cells, Experimental Cell Research, 2004, vol. 295, pp. 421-431.

Fabbro et al., Regulation of Tumor Suppressors by Nuclear-Cytoplasmic Shuttling, Experimental Cell Research, 2003, vol. 282, pp. 59-69.

Karpa et al., The Dopamine D3 Receptor Interacts with Itself and the Truncated D3 Splice Variant D3nf: D3-D3nf Interaction Causes Mislocalization of D3 Receptors, Molecular Pharmacology, 2000, vol. 58, No. 4, pp. 677-683.

Kent et al., The Comet Moment as a Measure of DNA Damage in the Comet Assay, Int. J. Radiat. Biol., 1995, vol. 67, No. 6, pp. 655-660.

Craig et al., A Masked NES in INI1/hSNF5 Mediates hCRM1-dependent Nuclear Export: Implications for Tumorigenesis, The EMBO Journal, 2002, vol. 21, Nos. 1 & 2, pp. 31-42.

* cited by examiner

SEQUENCE LISTING

<160> NUMBER OF SEQ ID NOS: 2

<210> SEQ ID NO 1
<211> LENGTH: 12
<212> TYPE: PRT
<213> ORGANISM: Homo sapiens

<400> SEQUENCE: 1

Asp Ile Leu Arg Asp Phe Phe Glu Leu Arg Leu Lys
1               5                   10

<210> SEQ ID NO 2
<211> LENGTH: 12
<212> TYPE: PRT
<213> ORGANISM: Homo Sapiens

<400> SEQUENCE: 2

Phe Ile Leu Glu Lys Ile Asp Gly Lys Ile Ile Ile
1               5                   10

NUCLEAR EXPORT INHIBITORS OF TOPOISOMERASE II ALPHA

CROSS REFERENCE TO RELATED APPLICATIONS

This application is a continuation of prior filed International Application, Serial Number PCT/US2009/067922 filed Dec. 14, 2009, which claims priority to U.S. provisional patent application No. 61/122,098 filed Dec. 12, 2008 which is hereby incorporated by reference into this disclosure.

FIELD OF INVENTION

This invention relates to the field of cancer therapy. More specifically, this invention relates to small molecules that inhibit the nuclear export of topoisomerase IIα. At least one of the disclosed molecules may be used as a chemotherapeutic agent or in a cocktail of drugs to treat cancer.

BACKGROUND OF THE INVENTION

Drug resistance, including resistance to topoisomerase II (topo II) inhibitors, is a major obstacle in the treatment of multiple myeloma. Topo II poisons that are used in the treatment of multiple myeloma include doxorubicin and etoposide (VP-16). Several mechanisms of resistance to topo IIα inhibitors have been described [Rasheed Z A, et al., *Oncogene* 2003; 22:7296-304; Oloumi A, et al., *Cancer Res* 2000; 60:5747-53]. Cell adhesion-mediated drug resistance and stromal cell adherence are important parameters in the local bone marrow environment in patients with multiple myeloma and appear to be major determinants of drug resistance [Hazlehurst L A, et al., *Blood* 2001; 98:1897-903; Hazlehurst L A, et al., *Cancer Res* 2006; 66:2338-45].

Human multiple myeloma cell density is a determinant of sensitivity to topo II inhibitors [Valkov N I, et al., *Br J Haematol* 2000; 108:331-45; Turner J G, et al., *J Cell Sci* 2004; 117:3061-71]. At increased cell densities, a considerable fraction of nuclear topo IIα is exported to the cytoplasm (>90%), resulting in reduced sensitivity to VP-16 and doxorubicin. This appears to occur both in human myeloma cell lines and in CD138+ cells isolated from patients with multiple myeloma. Nuclear export of topo IIα may contribute to drug resistance, and that resistance may not be due to differences in drug uptake, cell cycle, or cellular topo IIα protein levels [Valkov N I, et al., *Br J Haematol* 2000; 108:331-45; Turner J G, et al., *J Cell Sci* 2004; 117:3061-71]. The nuclear export signals for topo IIα are found at amino acids 1,017 to 1,028 and 1,054 to 1,066 [Turner J G, et al., *J Cell Sci* 2004; 117:3061-71]. Export can be blocked by treatment of the cells with leptomycin B, indicating that a CRM1-dependent pathway mediates export [Turner J G, et al., *J Cell Sci* 2004; 117:3061-71]. In the present study, we show that inhibition of CRM1-mediated export of topo IIα may render myeloma cells both in vitro and ex vivo more sensitive to topo II-targeted chemotherapy.

Use of CRM1 inhibition in cancer therapy has met with limited success. The first CRM1 inhibitor, leptomycin B, was found to efficiently inhibit nuclear export. However, leptomycin was found to have acute relative toxicities both in a human phase I trial [Newlands E S, et al., *Br J Cancer* 1996; 74:648-9] and in vitro. Leptomycin B in vitro studies found acute toxicity at concentrations<5 nmol/L for 1 hour. Therefore, in this study, we used the CRM1 inhibitor ratjadone C [Turner, J et al., *Cancer Research* (2009)69(17):6899-905; Falini B, et al., *Blood* (2006)107:4514-23]. Ratjadone C has been found to inhibit nuclear export without producing apoptosis or necrosis at concentrations up to 300 nmol/L for 48 h in an in vitro assay. However, ratjadone C prevents nuclear export of topo IIα; in this study, we show that ratjadone C also acutely sensitizes myeloma cells to the topo II inhibitors doxorubicin and VP-16. Additional low-toxicity CRM1 inhibitors are also being investigated by other laboratories and may become available for preclinical studies.

SUMMARY OF INVENTION

Twenty small molecule inhibitors (SMI) that bind to the two nuclear export sequences (NES) topo IIα have been identified from the NCI database using computer-generated molecular modeling. These SMI will improve the effectiveness of topo II directed therapeutics, particularly in the treatment of diseases such as multiple myeloma (MM). In vitro apoptosis assays indicate that these drugs may be effective as single agents or in combination with currently used cancer drugs that target topo II.

In a first aspect there is provided a method of treating cancer in a subject. The method includes the step of administering to the subject in need thereof an effective amount of a combination of a compound that binds a nuclear export signal (NES inhibitor) on topoisomerase IIα and a topoisomerase inhibitor. The NES inhibitor can be a small molecule inhibitor of nuclear export that binds to site 1 of the topoisomerase IIα molecule. In certain embodiments the NES inhibitor that binds site can be any of compounds A1 through A14, and combinations thereof, as disclosed in table 1. In an alternative embodiment the NES inhibitor can be a small molecule inhibitor of nuclear export that binds to site 2 of the topoisomerase IIα molecule. In particular embodiments the NES inhibitor that binds site 2 can be any of compounds B1-B10, and combinations thereof, as disclosed in table 1. In certain embodiments of the invention according to the first aspect the topoisomerase inhibitor can be doxorubicin, etoposide, etoposide phosphate, teniposide, epirubicin, daunomycin, amscrine or mitoxantrone. Moreover, in further embodiments the cancer to be treated can be multiple myeloma, breast cancer, ovarian cancer, testicular cancer, lung cancer, transitional cell bladder cancer, bronchogenic lung cancer, thyroid cancer, gastric cancer, soft tissue and osteogenic sarcomas, neuroblastoma, Wilms' tumor, malignant lymphoma (Hodgkin's and non-Hodgkin's), acute myeloblastic leukemia, acute lymphoblastic leukemia, or Kaposi's sarcoma. In an advantageous embodiment the cancer is multiple myeloma. The method can further include the steps of obtaining a sample from the patient and screening the sample for the cytoplasmic topo II α. Where cytoplasmic topo II α is detected the patient would be treated with an NES inhibitor, thus inhibiting the export of topo II α from the nucleus and enhancing efficacy of treatment with a topoisomerase inhibitor.

In a second aspect there is provided a method of inhibiting the nuclear export of topoisomerase IIα to the cytoplasm of a cell. The method includes the step of contacting the cell with one or more compounds that bind a nuclear export signal on topoisomerase IIα. The NES inhibitor can be a small molecule inhibitor of nuclear export that binds to site 1 of the topoisomerase IIα molecule. In certain embodiments the NES inhibitor that binds site can be any of compounds A1 through A14, and combinations thereof, as disclosed in table 1. In an alternative embodiment the NES inhibitor can be a small molecule inhibitor of nuclear export that binds to site 2 of the topoisomerase IIα molecule. In particular embodiments the NES inhibitor that binds site 2 can be any of compounds B1-B10, and combinations thereof, as disclosed in table 1.

In a third aspect there is provided a method of treating multiple myeloma in a patient. The method includes the step of administering to the subject in need thereof an effective amount of a combination of a compound that binds a nuclear export signal on topoisomerase IIα and a topoisomerase inhibitor The NES inhibitor can be a small molecule inhibitor of nuclear export that binds to site 1 of the topoisomerase IIα molecule. In certain embodiments the NES inhibitor that binds site can be any of compounds A1 through A14, and combinations thereof, as disclosed in table 1. In an alternative embodiment the NES inhibitor can be a small molecule inhibitor of nuclear export that binds to site 2 of the topoisomerase IIα molecule. In particular embodiments the NES inhibitor that binds site 2 can be any of compounds B1-B10, and combinations thereof, as disclosed in table 1. In certain embodiments of the invention according to the third aspect the topoisomerase inhibitor can be doxorubicin, etoposide, etoposide phosphate, teniposide, epirubicin, daunomycin, amscrine or mitoxantrone. The method can further include the steps of obtaining a sample from the patient and screening the sample for the of cytoplasmic topo II α. Where cytoplasmic topo II α is detected the patient would be treated with an NES inhibitor, thus inhibiting the export of topo II α from the nucleus and enhancing efficacy of treatment with a topoisomerase inhibitor.

In a fourth aspect there is provided a second method of treating cancer in a subject comprising the step of administering to the subject in need thereof an effective amount of a topoisomerase inhibitor and any of compounds A1 through A14, and combinations thereof, as disclosed in table 1. In certain embodiments of the invention according to the fourth aspect the topoisomerase inhibitor can be doxorubicin, etoposide, etoposide phosphate, teniposide, epirubicin, daunomycin, amscrine or mitoxantrone. The method can further include the steps of obtaining a sample from the patient and screening the sample for the of cytoplasmic topo II α. Where cytoplasmic topo II α is detected the patient would be treated with an NES inhibitor, thus inhibiting the export of topo II α from the nucleus and enhancing efficacy of treatment with a topoisomerase inhibitor. Moreover, in further embodiments the cancer to be treated can be multiple myeloma, breast cancer, ovarian cancer, testicular cancer, lung cancer, transitional cell bladder cancer, bronchogenic lung cancer, thyroid cancer, gastric cancer, soft tissue and osteogenic sarcomas, neuroblastoma, Wilms' tumor, malignant lymphoma (Hodgkin's and non-Hodgkin's), acute myeloblastic leukemia, acute lymphoblastic leukemia, or Kaposi's sarcoma. In an advantageous embodiment the cancer is multiple myeloma.

In a fifth aspect there is provided a third method of treating cancer in a subject. The method includes the steps of administering to the subject in need thereof an effective amount of a topoisomerase inhibitor and any of compounds A1 through A14, and combinations thereof, as disclosed in table 1. In certain embodiments of the invention according to the fourth aspect the topoisomerase inhibitor can be doxorubicin, etoposide, etoposide phosphate, teniposide, epirubicin, daunomycin, amscrine or mitoxantrone. Moreover, in further embodiments the cancer to be treated can be multiple myeloma, breast cancer, ovarian cancer, testicular cancer, lung cancer, transitional cell bladder cancer, bronchogenic lung cancer, thyroid cancer, gastric cancer, soft tissue and osteogenic sarcomas, neuroblastoma, Wilms' tumor, malignant lymphoma (Hodgkin's and non-Hodgkin's), acute myeloblastic leukemia, acute lymphoblastic leukemia, or Kaposi's sarcoma. In an advantageous embodiment the cancer is multiple myeloma. The method can further include the steps of obtaining a sample from the patient and screening the sample for the of cytoplasmic topo II α. Where cytoplasmic topo II α is detected the patient would be treated with an NES inhibitor, thus inhibiting the export of topo II α from the nucleus and enhancing efficacy of treatment with a topoisomerase inhibitor.

In a sixth aspect there is provided a fourth method of treating cancer in a subject. The method includes the steps of administering to the subject in need thereof an effective amount of a topoisomerase inhibitor and any of compounds B1 through B10, and combinations thereof, as disclosed in table 1. The method can further include the step of administering a topoisomerase inhibitor. The topoisomerase inhibitor can be doxorubicin, etoposide, etoposide phosphate, teniposide, epirubicin, daunomycin, amscrine or mitoxantrone. Moreover, in further embodiments the cancer to be treated can be multiple myeloma, breast cancer, ovarian cancer, testicular cancer, lung cancer, transitional cell bladder cancer, bronchogenic lung cancer, thyroid cancer, gastric cancer, soft tissue and osteogenic sarcomas, neuroblastoma, Wilms' tumor, malignant lymphoma (Hodgkin's and non-Hodgkin's), acute myeloblastic leukemia, acute lymphoblastic leukemia, or Kaposi's sarcoma. In an advantageous embodiment the cancer is multiple myeloma. The method can further include the steps of obtaining a sample from the patient and screening the sample for the of cytoplasmic topo II α. Where cytoplasmic topo II α is detected the patient would be treated with an NES inhibitor, thus inhibiting the export of topo II α from the nucleus and enhancing efficacy of treatment with a topoisomerase inhibitor.

In a seventh aspect there is provided a fifth method of treating cancer in a subject. The method includes the steps of administering to the subject in need thereof an effective amount of any of compounds A1 through A14, and combinations thereof, as disclosed in table 1. The method can further include the step of administering a topoisomerase inhibitor. The topoisomerase inhibitor can be doxorubicin, etoposide, etoposide phosphate, teniposide, epirubicin, daunomycin, amscrine or mitoxantrone. Moreover, in further embodiments the cancer to be treated can be multiple myeloma, breast cancer, ovarian cancer, testicular cancer, lung cancer, transitional cell bladder cancer, bronchogenic lung cancer, thyroid cancer, gastric cancer, soft tissue and osteogenic sarcomas, neuroblastoma, Wilms' tumor, malignant lymphoma (Hodgkin's and non-Hodgkin's), acute myeloblastic leukemia, acute lymphoblastic leukemia, or Kaposi's sarcoma. In an advantageous embodiment the cancer is multiple myeloma.

In a eighth aspect there is provided a combination therapy for the treatment of cancer. The combination therapy includes a compound that binds a nuclear export signal on topoisomerase IIα and a topoisomerase inhibitor. In certain embodiments the NES inhibitor is any of compounds A1 through A14, and combinations thereof, as disclosed in table 1. In further embodiments the NES inhibitor is any of compounds B1 through B10, and combinations thereof, as disclosed in table 1. The topoisomerase inhibitor can be doxorubicin, etoposide, etoposide phosphate, teniposide, epirubicin, daunomycin, amscrine or mitoxantrone.

In a ninth aspect there is provided a kit including any one of the combination therapies of the eighth aspect.

BRIEF DESCRIPTION OF THE DRAWINGS

For a fuller understanding of the invention, reference should be made to the following detailed description, taken in connection with the accompanying drawings, in which:

In FIG. 1A, H929, U266, and 8226 human myeloma cells grown at plateau (Plat) phase (high density) export topo IIα, whereas cells grown at log (Log) phase (low density) maintain topo IIα in the nucleus. Cells were grown for 16 hr at log or plateau densities and treated with 2 μmol/L doxorubicin for 4 h (n=2). Apoptosis was determined by caspase-3 staining with the use of flow cytometry (10,000 cells). Cells that maintained nuclear topo IIα were more sensitive to topo IIα-targeted chemotherapy. In FIG. 1B, cells grown at log- or plateau-phase conditions or cells treated with ratjadone C (RDC; 100 cells per experiment) were stained for topo IIα by fluorescence microscopy (n=2). Myeloma cells grown at log-phase conditions had the majority (≥90%) of the topo IIα in the nucleus, whereas plateau-phase cells exported topo IIα into the cytoplasm. The CRM1 inhibitor ratjadone C (5 nmol/L) was found to block export of topo IIα in cells grown in plateau-phase conditions.

In FIG. 3A, human myeloma cell lines 8226, H929, and U266 ($2 \times 10^6$ cells/mL) were incubated with the CRM1 inhibitor ratjadone C (RDC; 5 nmol/L) for 16 h. Cells were then treated with doxorubicin (Dox; 2 μmol/L) for 4 h and assayed for caspase-3 staining by flow cytometry. Cell lines were assayed in triplicate, and data from each drug combination were pooled. Ratjadone C versus control samples are statistically different (P=0.006) in A (control=1.50% and ratjadone C=3.84%). Ratjadone C was found to significantly (P=0.00005) sensitize cells to doxorubicin. In FIG. 3B, CRM1 inhibitor sensitizes ex vivo patient myeloma cells to doxorubicin. Bone marrow aspirates (n=7) obtained from multiple myeloma patients were treated with ratjadone C (5 nmol/L) for 16 h followed by doxorubicin (2 μmol/L) for 4 h and assayed for cleaved caspase-3 to determine apoptosis. Cells ($4 \times 10^6$/mL) treated with ratjadone C only were significantly different (P=0.03) from untreated cells (control=4.97% and ratjadone C=14.31%). Cells ($4 \times 10^6$/mL) treated with both ratjadone C and doxorubicin were significantly (P=0.0003) more sensitive to doxorubicin (3-fold) than doxorubicin alone. In FIG. 3C, mechanism of CRM1 and topo IIα inhibitor synergy. Human myeloma cell lines (n=9) were incubated at high density ($2 \times 10^6$/mL) for 16 h with the CRM1 inhibitor ratjadone C (5 nmol/L). Cell cultures were then exposed to the topo II-targeted agents VP-16 (10 μmol/L) for 8 h or doxorubicin (2 μmol/L) for 4 h and assayed for apoptosis with the terminal deoxynucleotidyl transferase-mediated dUTP nick end labeling assay (BD Pharmingen). CRM1 inhibition by ratjadone C increased the effectiveness of DNA-damaging agents to induce apoptosis. This effect was significant for doxorubicin/ratjadone C (P=0.00019) and VP-16/ratjadone C (P=0.0185). When topo IIα protein was reduced by topo IIα siRNA knockdown, apoptosis was substantially decreased, suggesting that apoptosis is topo IIα dependent.

In FIG. 4A, band depletion assay of the combination of ratjadone C (RDC) and VP-16 produced more DNA-topo IIα complexes, depleting the topo IIα band in the Western blot analysis. These data indicate that blocking nuclear export of topo IIα will increase the effectiveness of VP-16 and induce apoptosis. In FIG. 4B, comet assay of plateau-density H929 cells treated with ratjadone C (5 nmol/L) for 16 h and then with VP-16 (10 μmol/L) for 60 min. The comet moment of cells (50 per experiment) was assayed in two separate experiments for each drug combination and control samples. Comet assay is a measure of DNA cleavage. The CRM1 inhibitor ratjadone C increased DNA cleavage compared to the topo II inhibitor VP-16 alone (P=0.0006).

were selected for high-throughput molecular docking to identify human topo IIα-specific small molecules for functional assays.

Figure 9:
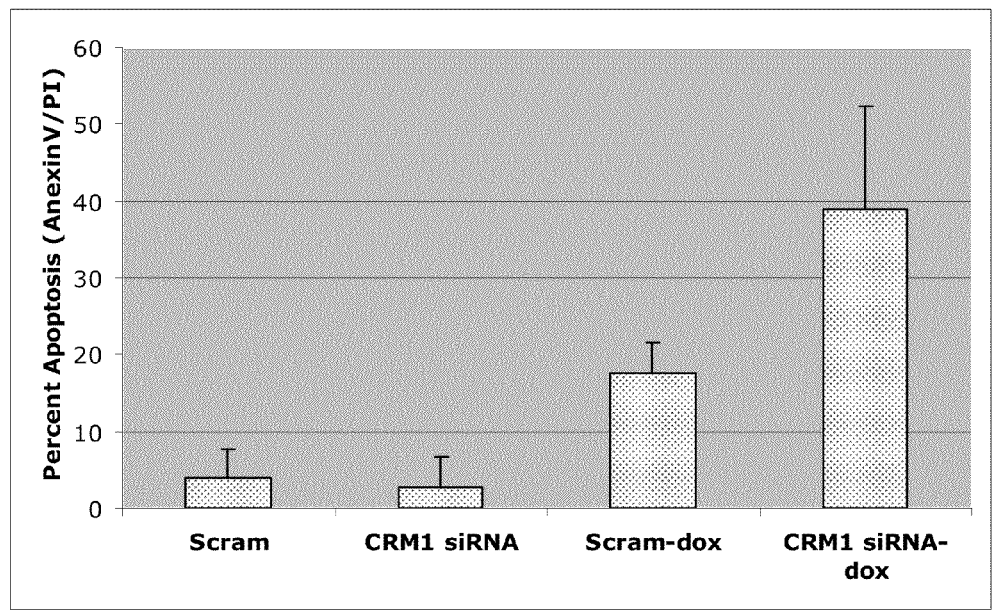

FIG. 9 is a graph showing CRM1 siRNA knockdown makes myeloma cells more sensitive to chemotherapy. Cells were transfected with siRNA, incubated at log-phase for 24 hours, and concentrated at plateau-phase conditions. At 48 hours cells were treated with the topo II inhibitor doxorubicin (1 µM) and assayed for apoptosis by Anexin V staining using flow cytometry.

Figure 10:
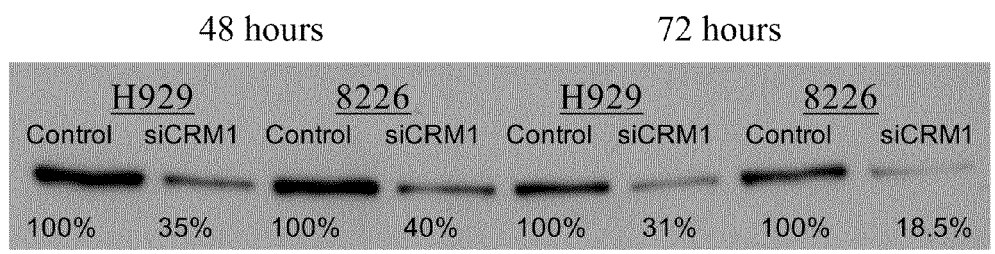

FIG. 10 is a western blot showing CRM1 siRNA knockdown.

Figure 11:
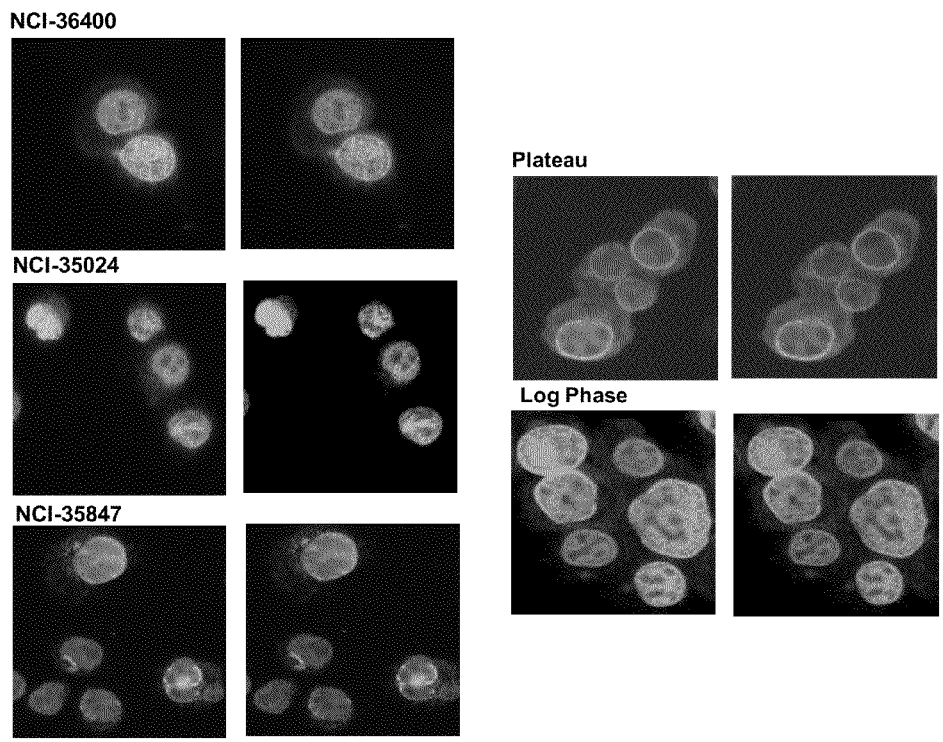

FIG. 11 is a series of images showing immunofluorescence microscopy of stained cells. Human MM cells were treated with 25 µM of each NES inhibitor and placed at plateau densities (2e6) for 20 hours. Cells were fixed and stained with DAPI (blue—not discernible in gray scale/found on images in the left column when viewed in color) and topo IIα antibody Kis1(green—discernable as light regions in the cells when shown in gray scale).

Figure 12:
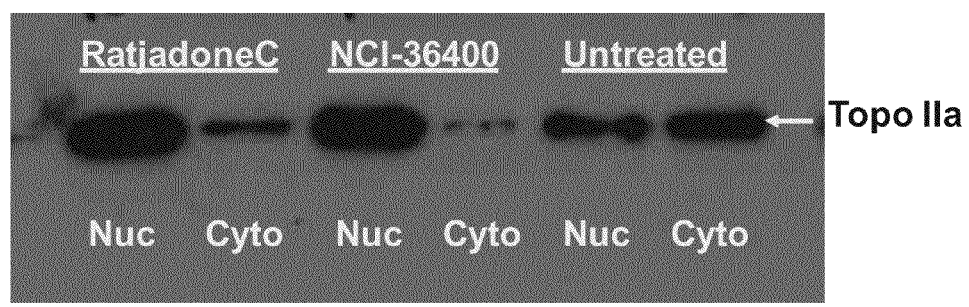

FIG. 12 is an image showing a fractionation experiment. The human multiple myeloma cell line NCI-H929 was incubated in the presence of either ratjadoneC, the small molecule inhibitor NCI-36400 or vehicle control for 20 hours at high-density conditions ($4\times10^6$ cells/114 RatjadoneC, a CRM1 inhibitor prevented nuclear export of topoisomerase IIα.into the cytoplasm. The small molecule inhibitor NCI-36400 also prevents topoisomerase IIα by blocking CRM1-topoisomerase IIα binding. The vehicle control sample exported topoisomerase IIα into the cytoplasm.

DETAILED DESCRIPTION OF THE PREFERRED EMBODIMENT

Topoisomerase IIα (topo IIα) is exported from the nucleus of human myeloma cells by a CRM1-dependent mechanism at cellular densities similar to those found in patient bone marrow. When topo IIα is trafficked to the cytoplasm, it is not in contact with the DNA. Thus, topo IIα inhibitors are unable to induce DNA-cleavable complexes and cell death. Using a CRM1 inhibitor or a CRM1-specific small interfering RNA (siRNA), nuclear export of topo IIα can be blocked as shown by immunofluorescence microscopy. Human myeloma cell lines and patient myeloma cells isolated from bone marrow were treated with a CRM1 inhibitor or CRM1-specific siRNA and exposed to doxorubicin or etoposide at high cell densities. CRM1-treated cell lines or myeloma patient cells were 4-fold more sensitive to topo II poisons as determined by an activated caspase assay. Normal cells were not significantly affected by CRM1-topo II inhibitor combination treatment. Cell death was correlated with increased DNA double-strand breaks as shown by the comet assay. Band depletion assays of CRM1 inhibitor-exposed myeloma cells showed increased topo IIα covalently bound to DNA. Topo IIα knockdown by a topo IIα-specific siRNA abrogated the CRM1-topo II therapy synergistic effect. These results suggest that blocking topo IIα nuclear export sensitizes myeloma cells to topo II inhibitors. This method of sensitizing myeloma cells provides a new therapeutic approach to multiple myeloma.

DEFINITIONS

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more doses. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

As used herein, "treatment" refers to obtaining beneficial or desired clinical results. Beneficial or desired clinical results include, but are not limited to, any one or more of: alleviation of one or more symptoms (such as tumor growth or metastasis), diminishment of extent of cancer, stabilized (i.e., not worsening) state of cancer, preventing or delaying spread (e.g., metastasis) of the cancer, delaying recurrence of cancer, delay or slowing of cancer progression, amelioration of the cancer state, and remission (whether partial or total). The methods of the invention contemplate any one or more of these aspects of treatment.

A "subject in need of treatment" is a mammal with cancer that is life-threatening or that impairs health or shortens the lifespan of the mammal.

A "pharmaceutically acceptable" component is one that is suitable for use with humans and/or animals without undue adverse side effects (such as toxicity, irritation, and allergic response) commensurate with a reasonable benefit/risk ratio.

A "safe and effective amount" refers to the quantity of a component that is sufficient to yield a desired therapeutic response without undue adverse side effects (such as toxicity, irritation, or allergic response) commensurate with a reasonable benefit/risk ratio when used in the manner of this invention.

A "pharmaceutically acceptable carrier" is a carrier, such as a solvent, suspending agent or vehicle, for delivering the compound or compounds in question to the animal or human. The carrier may be liquid or solid and is selected with the planned manner of administration in mind. Liposomes are also a pharmaceutical carrier. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

As used throughout the entire application, the terms "a" and "an" are used in the sense that they mean "at least one", "at least a first", "one or more" or "a plurality" of the referenced components or steps, unless the context clearly dictates otherwise. For example, the term "a cell" includes a plurality of cells, including mixtures thereof.

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range.

Other than in the operating examples, or unless otherwise expressly specified, all of the numerical ranges, amounts, values and percentages such as those for amounts of materials, times and temperatures of reaction, ratios of amounts, values for molecular weight (whether number average molecular weight ("$M_n$") or weight average molecular weight ("$M_w$"), and others in the following portion of the specification may be read as if prefaced by the word "about" even though the term "about" may not expressly appear with the value, amount or range. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used.

As used herein, the term "comprising" is intended to mean that the products, compositions and methods include the referenced components or steps, but not excluding others. "Consisting essentially of" when used to define products, compositions and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

As used herein, the term "pretreating", or "pretreatment", is intended to mean that a first treatment is administered prior to, or in conjunction with, a second treatment. In other words, the pretreatment may be performed before another, later treatment, thus allowing the pretreatment time to take effect. Alternatively, the pretreatment may be performed or administered simultaneously with a second treatment without a temporal delay. Advantageously, a pretreatment is administered prior to a second treatment. It is envisioned that pretreatment with an NES inhibitor can be performed 1 hr., 2 hrs., 4 hrs., 8 hrs., 1 day, 2 days, 4 days, 1 week, 2 weeks, or 1 month prior to treatment with an additional chemotherapeutic agent such as a topoisomerase inhibitor. Alternatively, the NES inhibitor may be co-administered or administered post-treatment in like intervals.

The present invention also provides a method for treating a patient, comprising administering to said patient simultaneously or sequentially a therapeutically effective amount of a combination of the anti-cancer NES inhibitor and a topoisomerase inhibitor. In one embodiment the patient is a human that is being treated for cancer. In different embodiments, the anti-cancer agent or treatment and NES inhibitor are co-administered to the patient in the same formulation; are co-administered to the patient in different formulations; are co-administered to the patient by the same route; or are co-administered to the patient by different routes. In another embodiment one or more other anti-cancer agents can additionally be administered to said patient with the anti-cancer agent/treatment and NES inhibitor combination. Furthermore, for any of the methods, compositions or kits of the invention described herein where an NES inhibitor is used, this invention also includes a corresponding method, composition or kit.

Kits for practicing the methods of the invention are further provided. By "kit" is intended any manufacture (e.g., a package or a container) comprising at least one reagent, e.g., an NES inhibitor of the invention. The kit may be promoted, distributed, or sold as a unit for performing the methods of the present invention. Additionally, the kits may contain a package insert describing the kit and methods for its use. Any or all of the kit reagents may be provided within containers that protect them from the external environment, such as in sealed containers or pouches.

In embodiments of any of the methods of treatment of the invention described herein, the cells to be treated may be relatively insensitive or refractory to treatment with the anti-cancer agent (e.g. topoisomerase inhibitor) or treatment as a single agent/treatment. It is envisioned that one or more NES inhibitors may be administered prior to or concurrently with treatment by the anti-cancer agent to enhance the agent's efficacy. Alternatively, the NES inhibitor may be used in treatment, without the topoisomerase inhibitor or other agent, as a single regimen.

The present invention also provides a kit comprising an NES inhibitor and a topoisomerase inhibitor. In an advantageous embodiment, the kit containers may further include a pharmaceutically acceptable carrier. The kit may further include a sterile diluent, which is preferably stored in a separate additional container. In another embodiment, the kit further comprises a package insert comprising printed instructions directing the use of a combined treatment of an NES inhibitor and the anti-cancer agent as a method for treating tumors, tumor metastases, or other cancers in a patient. The kit may also comprise additional containers comprising additional anti-cancer agents, agents that enhance the effect of such agents, or other compounds that improve the efficacy or tolerability of the treatment.

In the context of this invention, other cytotoxic, chemotherapeutic or anti-cancer agents, or compounds that enhance the effects of such agents, include, for example: alkylating agents or agents with an alkylating action, such as cyclophosphamide (CTX; e.g. CYTOXANϕ), chlorambucil (CHL; e.g. LEUKERAN®), cisplatin (Cis P; e.g. PLATINOL®) busulfan (e.g. MYLERAN®), melphalan, carmustine (BCNU), streptozotocin, triethylenemelamine (TEM), mitomycin C, and the like; anti-metabolites, such as methotrexate (MTX), etoposide (VP16; e.g. VEPESID®), 6-mercaptopurine (6 MP), 6-thioguanine (6TG), cytarabine (Ara-C), 5-fluorouracil (5-FU), capecitabine (e.g. XELODA®), dacarbazine (DTIC), and the like; antibiotics, such as actinomycin D, doxorubicin (DXR; e.g. ADRIAMYCIN®), daunorubicin (daunomycin), bleomycin, mithramycin and the like; alkaloids, such as vinca alkaloids such as vincristine (VCR), vinblastine, and the like; and other antitumor agents, such as paclitaxel (e.g. TAXOL®) and pactitaxel derivatives, the cytostatic agents, glucocorticoids such as dexamethasone (DEX; e.g. DECADRON®) and corticosteroids such as prednisone, nucleoside enzyme inhibitors such as hydroxyurea, amino acid depleting enzymes such as asparaginase, leucovorin and other folic acid derivatives, and similar, diverse antitumor agents. The following agents may also be used as additional agents: amifostine (e.g. ETHYOL®), dactinomycin, mechlorethamine (nitrogen mustard), streptozocin, cyclophosphamide, lomustine (CCNU), doxorubicin lipo (e.g. DOXIL®), gemcitabine (e.g. GEMZAR®), daunorubicin lipo (e.g. DAUNOXOME®), procarbazine, mitomycin, docetaxel (e.g. TAXOTERE®), aldesleukin, carboplatin, oxaliplatin, cladribine, camptothecin, CPT 11 (irinotecan), 10-hydroxy 7-ethyl-camptothecin (SN38), floxuridine, fludarabine, ifosfamide, idarubicin, mesna, interferon beta, interferon alpha, mitoxantrone, topotecan, leuprolide, megestrol, melphalan, mercaptopurine, plicamycin, mitotane, pegaspargase, pentostatin, pipobroman, plicamycin, tamoxifen, teniposide, testolactone, thioguanine, thiotepa, uracil mustard, vinorelbine, chlorambucil.

As used herein, the term "patient" preferably refers to a human in need of treatment with an anti-cancer agent or treatment for any purpose, and more preferably a human in need of such a treatment to treat cancer, or a precancerous condition or lesion. However, the term "patient" can also refer to non-human animals, preferably mammals such as dogs, cats, horses, cows, pigs, sheep and non-human primates, among others, that are in need of treatment with an anti-cancer agent or treatment.

In a preferred embodiment, the patient is a human in need of treatment for cancer, or a precancerous condition or lesion, wherein the cancer is preferably multiple myeloma, breast cancer, ovarian cancer, transitional cell bladder cancer, bronchogenic lung cancer, thyroid cancer, gastric cancer, soft tissue and osteogenic sarcomas, neuroblastoma, Wilms' tumor, malignant lymphoma (Hodgkin's and non-Hodgkin's), acute myeloblastic leukemia, acute lymphoblastic leukemia, Kaposi's sarcoma related to acquired immunodeficiency syndrome (AIDS), bladder cancer, head and neck cancer, liver cancer, lung cancer, lymphomas, mesothelioma, neuroblastoma, ovarian cancer, pancreatic cancers, prostate cancer, sarcomas, stomach cancer, testicular cancers (germ cell), thyroid cancer, cancer of the uterus. However, cancers that may be treated by the methods described herein include lung cancer, bronchioloalveolar cell lung cancer, bone cancer, skin cancer, cancer of the head or neck, cutaneous or intraocular melanoma, uterine cancer, ovarian cancer, rectal cancer, cancer of the anal region, stomach cancer, gastric cancer, uterine cancer, carcinoma of the fallopian tubes, carcinoma of the endometrium, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the ureter, carcinoma of the renal pelvis, mesothelioma, hepatocellular cancer, biliary cancer, cancer of the kidney, renal cell carcinoma, chronic or acute leukemia, lymphocytic lymphomas, neoplasms of the central nervous system (CNS), spinal axis tumors, brain stem glioma, glioblastoma multiforme, astrocytomas, schwannomas, ependymomas, medulloblastomas, meningiomas, squamous cell carcinomas, pituitary adenomas, NSCL, pancreatic, head and neck, colon, prostate, endometrial, renal, bladder, ovarian or breast cancer, or a glioblastoma, fibrosarcoma, or melanoma. including refractory versions of any of the above cancers, or a combination of one or more of the above cancers.

The term "refractory" as used herein is used to define a cancer for which treatment (e.g. chemotherapy drugs, biological agents, and/or radiation therapy) has proven to be ineffective. A refractory cancer tumor may shrink, but not to the point where the treatment is determined to be effective. Typically however, the tumor stays the same size as it was before treatment (stable disease), or it grows (progressive disease).

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

The anti-cancer agent or treatment will typically be administered to the patient in a dose regimen that provides for the most effective treatment of the cancer (from both efficacy and safety perspectives) for which the patient is being treated, as known in the art. In conducting the treatment method of the present invention, the anti-cancer agent or treatment can be administered in any effective manner known in the art, such as by oral, topical, intravenous, intra-peritoneal, intramuscular, intra-articular, subcutaneous, intranasal, intra-ocular, vaginal, rectal, or intradermal routes, depending upon the type of cancer being treated, the type of anti-cancer agent or treatment being used, and the medical judgment of the prescribing physician as based, e.g., on the results of published clinical studies. When the anti-cancer agent or treatment is radiation or a radiochemical, the agent or treatment can be administered in any effective manner known in the art, as described briefly herein, above.

The anti-cancer agent or treatment can be administered with various pharmaceutically acceptable inert carriers in the form of tablets, capsules, lozenges, troches, hard candies, powders, sprays, creams, salves, suppositories, jellies, gels, pastes, lotions, ointments, elixirs, syrups, and the like. Administration of such dosage forms can be carried out in single or multiple doses. Carriers include solid diluents or fillers, sterile aqueous media and various non-toxic organic solvents, etc. Oral pharmaceutical compositions can be suitably sweetened and/or flavored.

The anti-cancer agent or treatment can be combined together with various pharmaceutically acceptable inert carriers in the form of sprays, creams, salves, suppositories, jellies, gels, pastes, lotions, ointments, and the like. Administration of such dosage forms can be carried out in single or multiple doses. Carriers include solid diluents or fillers, sterile aqueous media, and various non-toxic organic solvents, etc.

Methods of preparing pharmaceutical compositions comprising anti-cancer agents or treatments are known in the art. Methods of preparing pharmaceutical compositions are also known in the art. In view of the teaching of the present invention, methods of preparing pharmaceutical compositions comprising both a anti-cancer agent or treatment and an NES inhibitor that sensitizes tumor cells to the pro-apoptotic effects of the anti-cancer agent or treatment will be apparent from the art, from other known standard references, such as Remington's Pharmaceutical Sciences, Mack Publishing Company, Easton, Pa., $18^{th}$ edition (1990).

For oral administration of the anti-cancer agent or treatment or the NES inhibitor that sensitizes cells to the pro-apoptotic effects of the anti-cancer agent or treatment, tablets containing one or both of the active agents are combined with any of various excipients such as, for example, micro-crystalline cellulose, sodium citrate, calcium carbonate, dicalcium phosphate and glycine, along with various disintegrants such as starch (and preferably corn, potato or tapioca starch), alginic acid and certain complex silicates, together with granulation binders like polyvinyl pyrrolidone, sucrose, gelatin and acacia. Additionally, lubricating agents such as magnesium stearate, sodium lauryl sulfate and talc are often very useful for tableting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, active agents may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration of either or both of the active agents, solutions in either sesame or peanut oil or in aqueous propylene glycol may be employed, as well as sterile aqueous solutions comprising the active agent or a corresponding water-soluble salt thereof. Such sterile aqueous solutions are preferably suitably buffered, and are also preferably rendered isotonic, e.g., with sufficient saline or glucose. These particular aqueous solutions are especially suitable for intravenous, intramuscular, subcutaneous and intraperitoneal injection purposes. The oily solutions are suitable for intra-articular, intramuscular and subcutaneous injection purposes. The preparation of all these solutions under sterile conditions is readily accomplished by standard pharmaceutical techniques well known to those skilled in the art.

Topoisomerase Inhibitors

Topoisomerase inhibitors are agents designed to interfere with the action of topoisomerase enzymes (topoisomerase I and II), which are enzymes that control the changes in DNA structure by catalyzing the breaking and rejoining of the phosphodiester backbone of DNA strands during the normal cell cycle. Topoisomerases have become popular targets for cancer chemotherapy treatments. It is thought that topoisomerase inhibitors block the ligation step of the cell cycle, generating single and double stranded breaks that harm the integrity of the genome. Introduction of these breaks subsequently lead to apoptosis and cell death. Topoisomerase inhibitors are often divided according to which type of enzyme it inhibits. Topoisomerase I is targeted by topotecan, irinotecan, lurtotecan and exatecan, each of which is commercially available from. Topotecan is available from GlaxoSmithKline under the trade name Hycamtim®. Irinotecan is available from Pfizer under the trade name Camptosar®. Lurtotecan may be obtained as a liposomal formulation from Gilead Sciences Inc. Topoisomerase inhibitors may be administered at an effective dose. In some embodiments an effective dose for treatment of a human will be in the range of about 0.01 to about 10 $mg/m^2/day$. The treatment may be repeated on a daily, bi-weekly, semi-weekly, weekly, or monthly basis. In some embodiments, a treatment period may be followed by a rest period of from one day to several days, or from one to several weeks. In combination with an NES inhibitor, the NES inhibitor and the topoisomerase inhibitor may be dosed on the same day or may be dosed on separate days.

Compounds that target type II topoisomerase are split into two main classes: topoisomerase poisons, which target the topoisomerase-DNA complex, and topoisomerase inhibitors, which disrupt catalytic turnover. Topo II poisons include but are not limited to eukaryotic type II topoisomerase inhibitors (topo II): amscrine, etoposide, etoposide phosphate, teniposide and doxorubicin. These drugs are anti-cancer therapies. Examples of topoisomerase inhibitors include ICRF-193. These inhibitors target the N-terminal ATPase domain of topo II and prevent topo II from turning over. The structure of this compound bound to the ATPase domain has been solved by Classen (Proceedings of the National Academy of Science, 2004) showing that the drug binds in a non-competitive manner and locks down the dimerization of the ATPase domain.

Clinical Efficacy

Clinical efficacy may be measured by any method known in the art. In some embodiments, clinical efficacy of the combination of topoisomerase inhibitor and NES inhibitor may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD≥6 months. The CBR for combination therapy with a topoisomerase inhibitor and a NES inhibitor may be compared to that of therapy with topoisomerase inhibitor alone ($CBR_T$). In some embodiments, $CBR_{T-B}$ is at least about 40%, at least about 50% or at least about 60%.

In some embodiments disclosed herein, the methods include predetermining that a cancer is treatable by NES inhibitor. Some such methods comprise identifying a level of topo IIα in a tumor sample of a patient, determining whether the level of topo IIα expression in the sample is greater than a predetermined value, evaluating the distribution of topo IIα within the cells of the sample (i.e. nuclear vs. cytoplasmic), and treating the patient with a combination of a topoisomerase inhibitor (such as topotecan or irinotecan) and an NES inhibitor. In evaluating the distribution of topo II α, comparisons can be made between the levels of cytoplasmic and/or nuclear topo II α with one or more standards for these levels.

In some embodiments, the effective dose of topoisomerase inhibitor used with a NES inhibitor may be about 10 to about 90%, about 10 to about 80%, about 10 to about 60%, about 10 to about 50%, less than about 90%, less than about 80%, less than about 60%, less than about 50% or less than about 40% of an effective dose of the topoisomerase inhibitor used alone.

Unless defined otherwise, all technical and scientific terms used herein have the same meaning as commonly understood by one of ordinary skill in the art (e.g., in cell culture, molecular genetics, nucleic acid chemistry, hybridisation techniques and biochemistry). Standard techniques are used for molecular, genetic and biochemical methods. See, generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) 4th Ed, John Wiley & Sons, Inc.; as well as Guthrie et al., Guide to Yeast Genetics and Molecular Biology, Methods in Enzymology, Vol. 194, Academic Press, Inc., (1991), PCR Protocols: A Guide to Methods and Applications (Innis, et al. 1990. Academic Press, San Diego, Calif.), McPherson et al., PCR Volume 1, Oxford University Press, (1991), Culture of Animal Cells: A Manual of Basic Technique, 2nd Ed. (R. I. Freshney. 1987. Liss, Inc. New York, N.Y.), and Gene Transfer and Expression Protocols, pp. 109-128, ed. E. J. Murray, The Humana Press Inc., Clifton, N.J.).

The following examples are provided for the purpose of illustration and are not intended to limit the scope of the present invention.

Example 1

CRM1 Inhibition Sensitizes Human Multiple Myeloma Cells to Topoisomerase II Inhibitors The intracellular location of a protein may be at least as important as its expression. Diseases as dissimilar as cystic fibrosis, schizophrenia [Karpa K D, et al., *Mol Pharmacol* (2000)58:677-83], nephrogenic diabetes insipidus, and many types of cancers, as reviewed previously [Davis J R, et al., *Pharm Res* (2007)24:17-27], may be caused by intracellular mislocalization of individual proteins. Specific examples of proteins that must be in the nucleus to prevent cancer initiation, progression, or chemotherapeutic response include p53 [Fabbro M, et al., *Exp Cell Res* (2003)282:59-69], galectin-3 [Takenaka Y, et al., *Mol Cell Biol* (2004)24:4395-406], FOXO [Nakamura N, et al., *Mol Cell Biol* (2000)20:8969-82], INI1/hSNPF5 [Craig E, et al., *EMBO J* (2002)21:31-42], p27$^{Kip1}$ [Min Y H, et al., *Cancer Res* (2004)64:5225-31], p21$^{Cip1}$, and topo IIα [Valkov N I, et al., *Br J Haematol* (2000)108:331-45; Turner J G, et al., *J Cell Sci* (2004)117: 3061-71]. Mislocalization of a protein can render it ineffective as a tumor suppressor or as a target for chemotherapy. However, it is possible that blocking nuclear export of any or all of these proteins may induce tumor suppression or apoptosis or, in the case of topo IIα, may reverse drug resistance to topo IIα inhibitors. Multiple myeloma is one such example, where the cells possess a CRM1-mediated mechanism in which topo IIα is exported from the nucleus and away from the DNA, rendering topo II inhibitors ineffective to produce cleavable complexes and DNA strand breaks.

Myeloma cells, under high-density conditions, will export topo IIα into the cytoplasm both in vivo and in vitro [Valkov N I, et al., *Br J Haematol* (2000)108:331-45; Turner J G, et al., *J Cell Sci* (2004)117:3061-71]. Nuclear export of topo IIα contributes to drug resistance and that the resistance was not due to differences in drug uptake, cell cycle, or total cellular topo IIα protein levels. In addition, topo IIα nuclear export has been shown to be CRM1 mediated, and topo IIα protein has been found to contain two functional nuclear export signals at amino acids 1,017 to 1,028 and 1,054 to 1,066 [Turner J G, et al., *J Cell Sci* (2004)117:3061-71]. Export by both signals was blocked by treatment of the cells with leptomycin B, indicating that a CRM1-dependent pathway mediates export. Leptomycin B has been shown to be too toxic for clinical use [Newlands E S, et al., *Br J Cancer* (1996)74:648-9]; however, less toxic CRM1 inhibitors may alleviate these problems.

Figure 1:
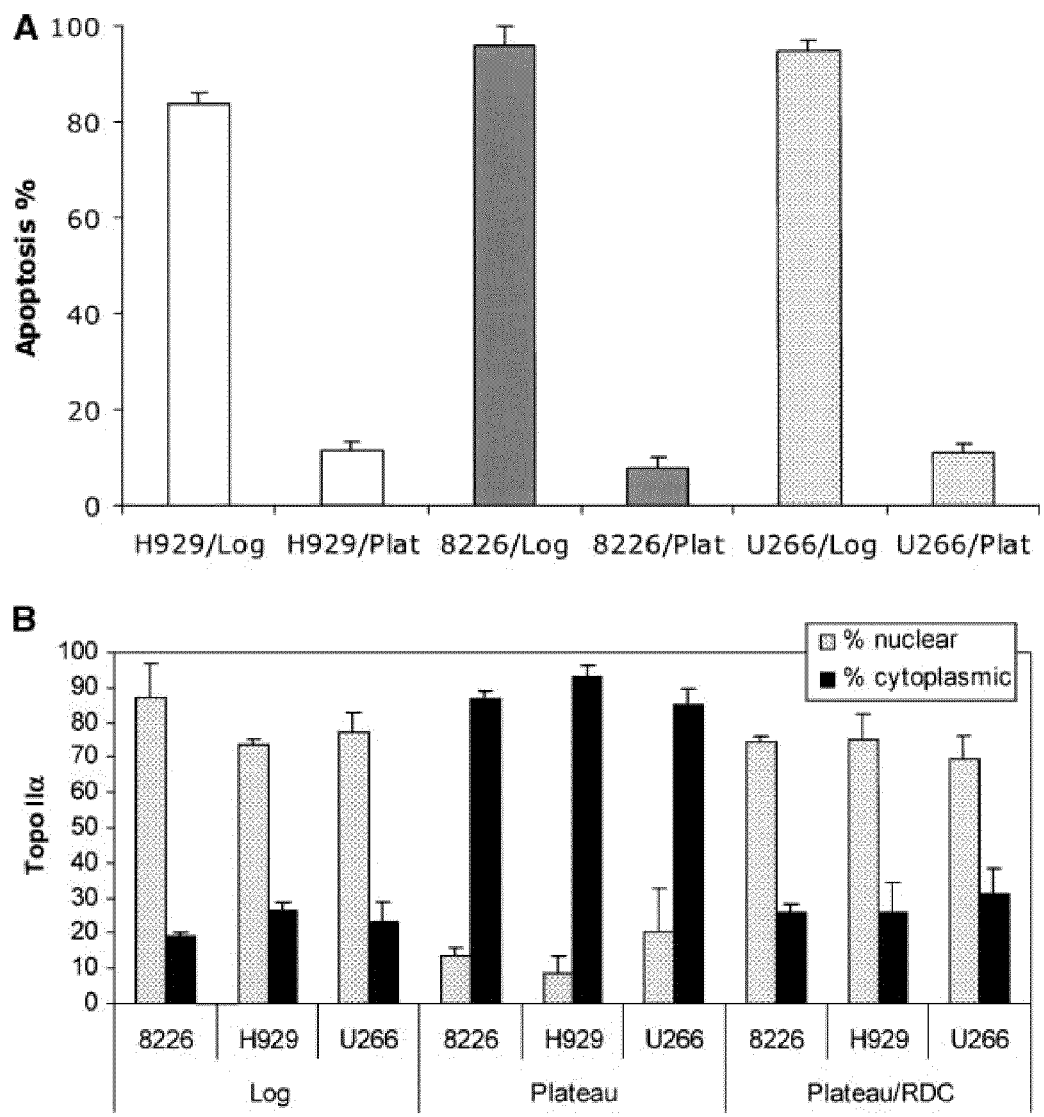
FIG. 1 shows intracellular trafficking of topo IIα in log- and plateau-density myeloma cells.
Figure 2:
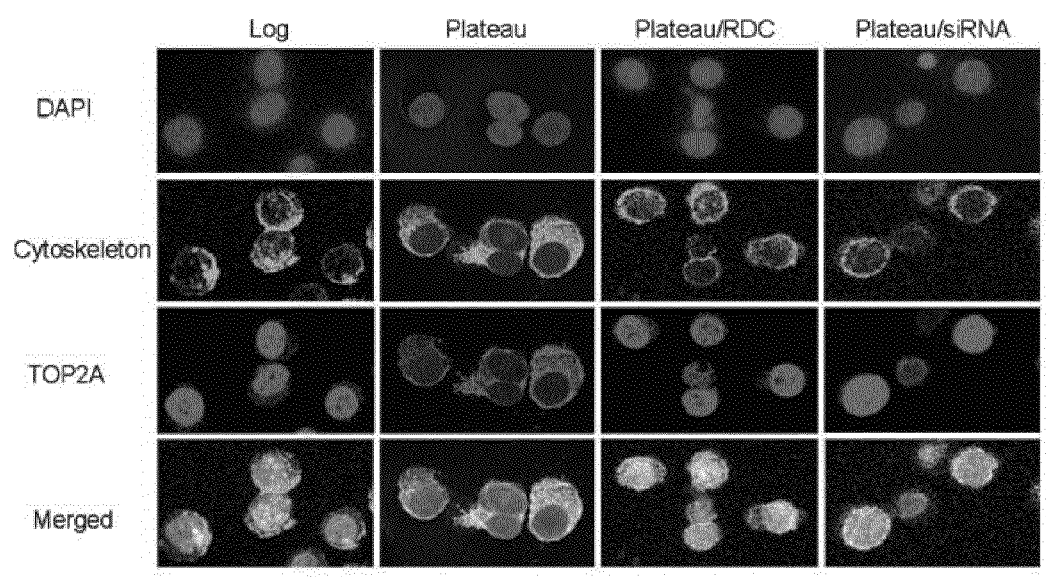
FIG. 2 shows H929 topo IIα immunofluorescence. H929 human myeloma cells were grown at log and plateau densities, fixed with 4% paraformaldehyde, permeabilized with 0.25% Triton X-100, and stained for cytoskeletal protein (phalloidin; green when viewed in color), topo IIα (TOP2A; red when viewed in color), and DNA (DAPI; blue when viewed in color). Results indicate that topo IIα is present in the nucleus of log-density cells and is exported from the nucleus in plateau-density cells. However, nuclear export is blocked in plateau cells by the CRM1 inhibitor ratjadone C (RDC) and by transfection with CRM1-specific siRNA. Under the conditions of this experiment, CRM1 siRNA knockdown was 69%.
Figure 3:
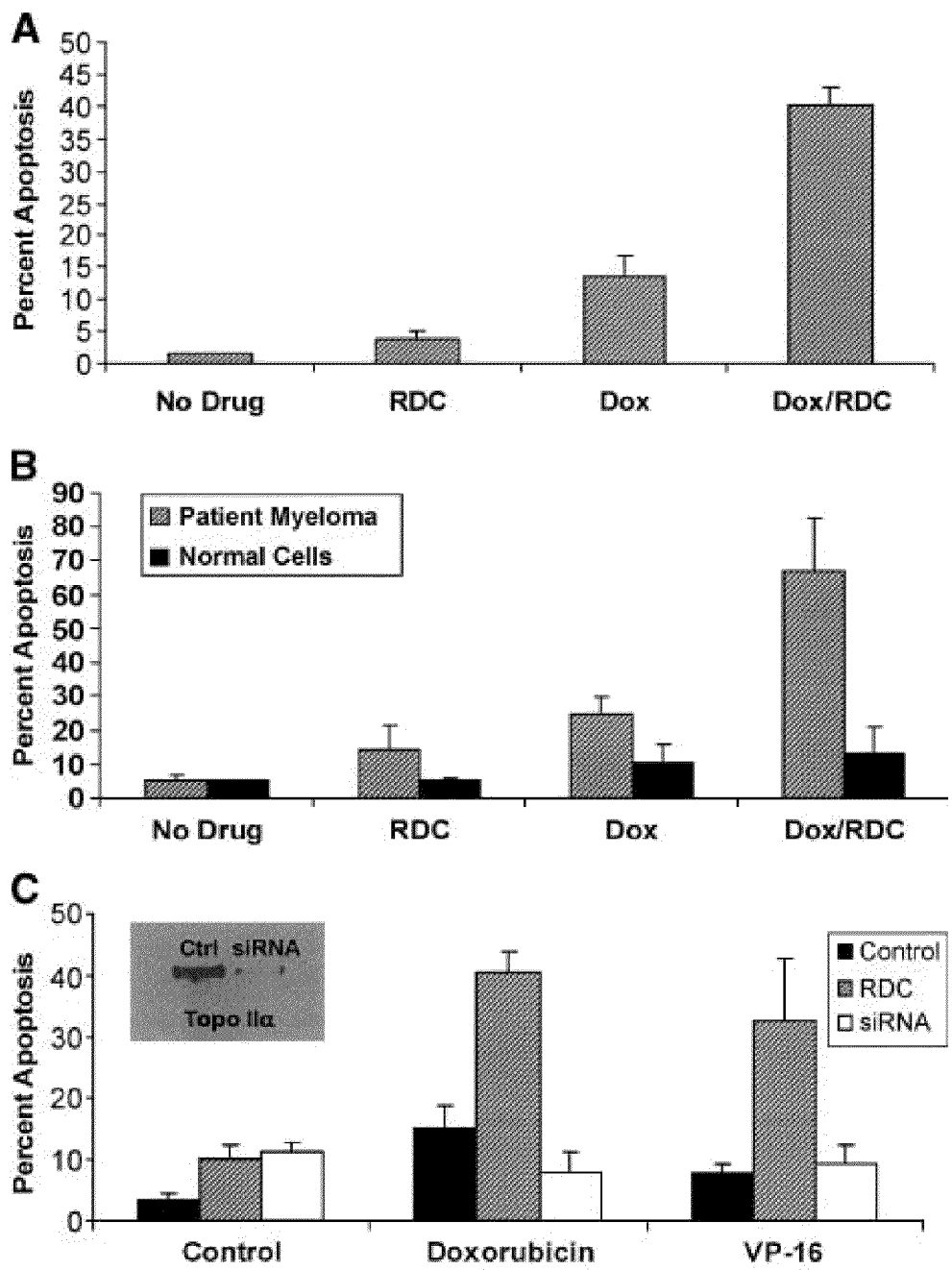
FIG. 3 is a series of graphs that show CRM1 inhibitor sensitizes myeloma cells to doxorubicin.
Figure 4:
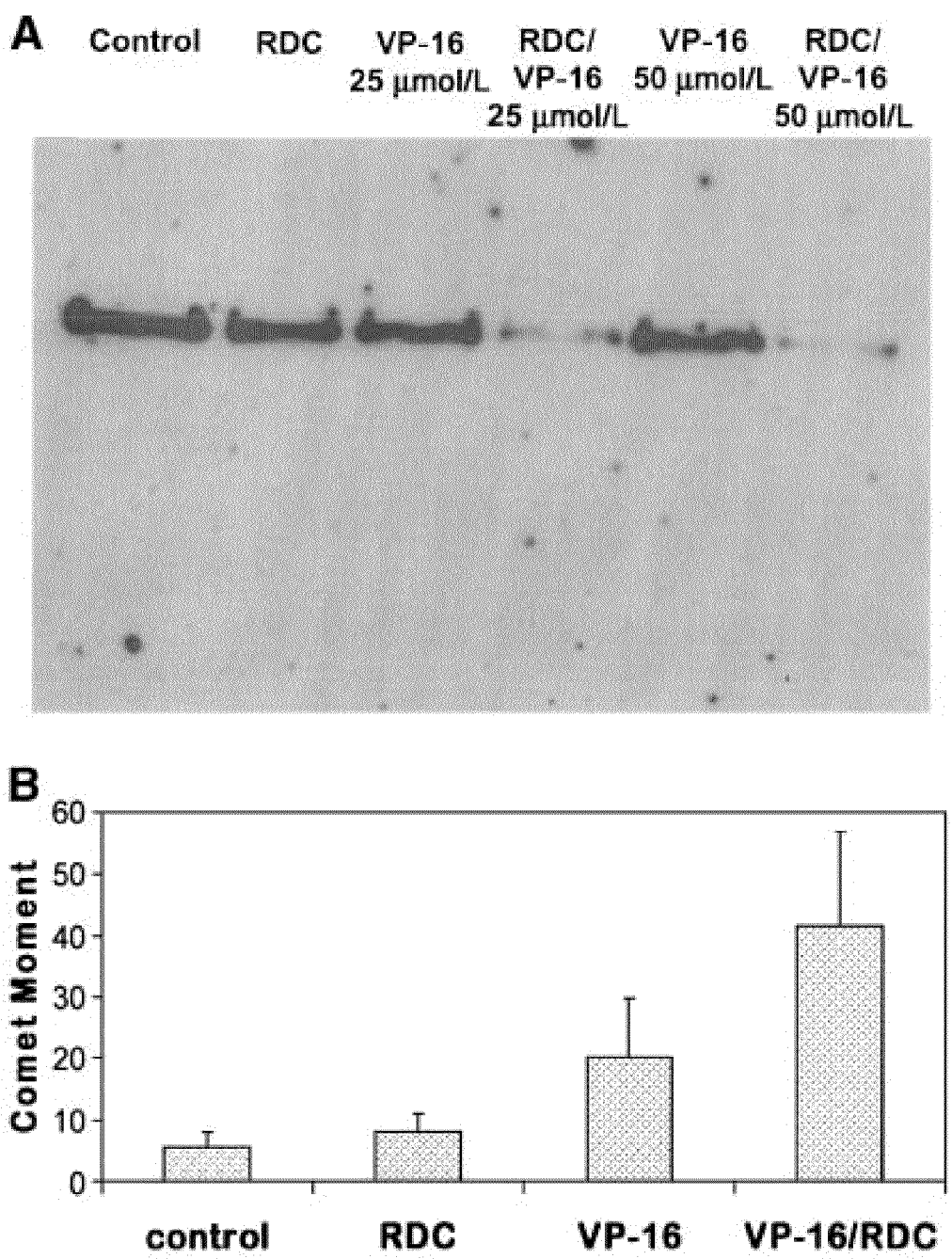
FIG. 4 shows the results of band depletion and comet assay.

It is shown herein that myeloma cells grown at high density are highly resistant to topo II-directed chemotherapeutic drugs (FIG. 1A) and that drug resistance correlated with nuclear export of topo IIα (FIGS. 1B and 1C). Based on these data, we proposed that blocking CRM1-mediated export of topo IIα may make myeloma cells more sensitive to topo II-active agents. To evaluate whether blocking topo IIα export would sensitize cells, we knocked down CRM1 mRNA and protein expression in cells by transfection with CRM1-specific siRNAs and by using the CRM1-inhibiting drug ratjadone C. Ratjadone C is a potent inhibitor of CRM1, has been shown to have anticancer properties, and has reduced toxicity in vitro compared to leptomycin B when used at low concentrations [Falini B, et al., *Blood* (2006)107:4514-23]. CRM1 inhibition by siRNA and ratjadone C in human myeloma cells was found to prevent nuclear export of topo IIα in plateau-density cell cultures (FIGS. 1B and 2). Depletion or inhibition of CRM1 by siRNA or ratjadone C caused high-density myeloma cells to become 4-fold more sensitive to the topo II inhibitors doxorubicin and VP-16 as measured by apoptosis (FIGS. 4A-C). Depletion of topo IIα protein by specific topo IIα siRNA knockdown reversed this synergistic effect, indicating that topo IIα was the targeted molecule for CRM1 synergistic activity (FIG. 3C). In addition, it was found that blocking CRM1-mediated export sensitized patient myeloma cells obtained from bone marrow aspirates to the topo II poison doxorubicin. Normal peripheral blood mononuclear cells were not sensitized by CRM1 inhibition. One explanation is that these cells were not sensitized because they are not replicating at a high rate, unlike the myeloma cells, which double approximately every 24 h. In addition, normal cells do not export topo IIα. Therefore, ratjadone C treatment would not affect intracellular localization.

Figure 5:
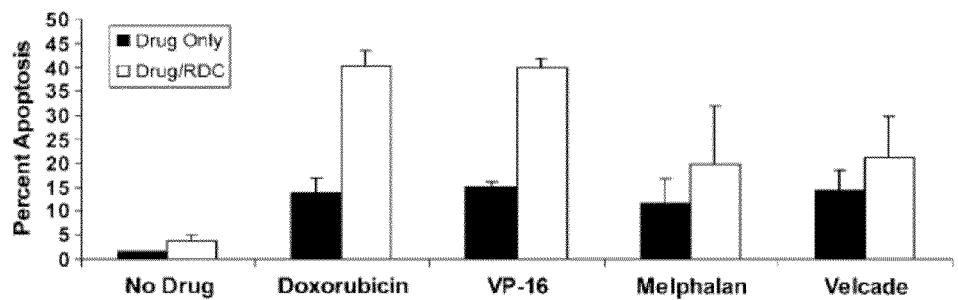
FIG. 5 is a graph showing the additional drug combinations in H929 and 8226 human myeloma cell lines. H929 and 8226 human myeloma cell lines were placed at high density ($4 \times 10^6$) with and without 5 nmol/L ratjadone C (RDC) and incubated for 16 h (n=4 for each cell line). Cells were then incubated for 4 h with one of the following: 2 μmol/L doxorubicin, 10 μmol/L VP-16, 10 μmol/L melphalan, or 10 μmol/L Velcade. CRM1 inhibition by ratjadone C sensitized myeloma cells to the topo IIα inhibitors doxorubicin (P=0.00005) and VP-16 (P=0.02) but not myeloma cells treated with melphalan (P=0.35) or Velcade (P=0.30).

When additional drugs were used in combination with ratjadone C, it was found that myeloma cells were sensitized to the topo II inhibitors doxorubicin and VP-16 but not to the alkylating agent melphalan or to the proteosome inhibitor Velcade (FIG. 5).

Thus, maintaining topo IIα in the nucleus by inhibition of CRM1 greatly enhanced the cytotoxic effect of the topo II inhibitors doxorubicin and VP-16 in high-density myeloma cells. Band depletion assays indicated that more DNA-topo IIα complexes were stabilized in cells when CRM1 was inhibited (FIG. 4A), and these increased cleavable complexes resulted in increased strand breaks as measured by the comet assay (FIG. 4B) and subsequent apoptosis. These findings show the therapeutic value in the treatment of multiple myeloma.

Materials and Methods

Cell lines: Human myeloma cell lines NCI-H929 (H929) and RPMI-8226 (8226) were newly obtained from the American Type Culture Collection. U266B1 (U266) human myeloma cell lines were provided by Dr. Lori Hazlehurst (H. Lee Moffitt Cancer Center). All cell lines were grown in RPMI 1640 containing 100 units/mL penicillin, 100 μg/mL streptomycin (Invitrogen), and 10% fetal bovine serum (Hyclone) at 37° C. and 5% $CO_2$. H929 cell medium required the addition of 0.025% β-mercaptoethanol (Sigma).

Cell density and drug treatment: The model used to assay density-dependent protein trafficking involved incubating cells at high- and low-density culture conditions. It has previously been shown that cells grown at different densities exhibit specific characteristics such as drug resistance and nuclear-cytoplasmic trafficking of topo IIα [Valkov N I, et al. *Br J Haematol* (2000)108:331-45; Turner J G, et al., *J Cell Sci* (2004)117:3061-71]. Human myeloma cell lines (8226, H929, and 0266) grown at $2 \times 10^5$ cells/mL were defined as low density (log phase), and cells grown at $2\times10^6$ cells/mL were defined as high density (plateau phase). Cell lines were placed at log- and plateau-density conditions and incubated with and without the highly specific CRM1 inhibitor ratjadone C [Falini B, et al., *Blood* (2006)107:4514-23] or were transfected with CRM1 200 nmol/L small interfering RNA (siRNA; Dharmacon). Ratjadones are naturally occurring antibiotics isolated from myxobacteria. Ratjadone C is a potent inhibitor of CRM1 and prevents nuclear export by alkylating the active site $Cys^{528}$ amino acid residue of CRM1. Ratjadone C has been shown to have anticancer properties and has reduced toxicity in vitro compared to leptomycin B. To determine the concentration of ratjadone C to use, ratjadone C was titrated to find the lowest concentration that would inhibit nuclear export of topo II in myeloma cell lines H929 and 8226. The concentration arrived at was ~5 nmol/L; all ratjadone C experiments used this concentration. Cells were treated with ratjadone C for 16 h followed by doxorubicin (2 μmol/L; Sigma) for 4 h or VP-16 (10 μmol/L; Sigma) for 8 h and assayed for apoptosis by either anti-caspase-3 or terminal deoxynucleotidyl transferase-mediated dUTP nick end labeling staining (BD Pharmingen).

CRM1 inhibitor sensitizes patient myeloma cells to topo II drugs: Human bone marrow aspirates obtained from multiple myeloma patients were collected using a protocol approved by the University of South Florida Institutional Review Board. Patient samples were assayed for percentage of plasma cells by toluidine blue staining and microscopy. Cells used for assay consisted of between 75% and 90% plasma cells isolated by Ficoll gradient centrifugation. Cells ($4\times10^6$/mL) were treated with ratjadone C (5 nmol/L) for 16 h followed by doxorubicin (2 μmol/L) for 4 h and assayed for apoptosis by anti-caspase-3 (BD Pharmingen).

siRNA knockdown and Western blot: All electroporation transfections were done in a freshly made transfection buffer containing 120 mmol/L potassium chloride (Sigma), 0.15 mmol/L calcium chloride, 10 mmol/L potassium phosphate (pH 7.6), 25 mmol/L HEPES, 2 mmol/L EGTA (pH 7.6), 5 mmol/L magnesium chloride, 2 mmol/L ATP (pH 7.6), 5 mmol/L glutathione, 1.25% DMSO, and 50 mmol/L trehalose (Sigma). Each transfection used $3\times10^6$ myeloma cells. Cells were washed two times in PBS and placed in a 200 μL volume of transfection buffer. CRM1-specific siRNA (Dharmacon), scramble control siRNA (Dharmacon), or topo IIα-specific siRNA (Ambion) was added (200 nmol/L); the sample was then placed in a 2 mm electroporation cuvette and transfected at 140 V and 975 μF in a Bio-Rad GenePulser Xcell electroporation unit (Bio-Rad). Transfected cells were incubated in the cuvette for 15 min at 37° C. in a 5% $CO_2$ incubator and transferred to a sterile T25 tissue culture flask, and 10 mL fresh medium was added. After 48 h, the transfected cells were harvested by centrifugation at 500×g for 5 min, washed with cold PBS, and lysed by sonication (40% duty cycle, 7 bursts) in SDS buffer [2% SDS, 10% glycerol, 60 mmol/L Tris (pH 6.8)]. Protein from $2\times10^5$ cells per lane was separated on 8% SDS-PAGE gels and transferred to polyvinylidene difluoride membranes (Amersham) overnight (30 V at 4° C.) with the use of a Bio-Rad Mini-Transblot apparatus. Membranes were blocked for 1 h at ambient temperature in a blocking buffer containing 0.1 mol/L Tris-HCl, 0.9% NaCl, and 0.5% Tween 20 (TBST) and 5% nonfat dry milk. CRM1 was identified by incubation in a 1:1,000 dilution of H-300 antibody (Santa Cruz Biotechnology) in blocking buffer overnight at 4° C. Membranes were washed three times for 10 min in TBST and incubated for 1 h with goat anti-rabbit polyclonal IgG antibody linked to a horseradish peroxidase antibody (Sigma) in blocking buffer at a 1:2,000 dilution. Antibody binding was visualized by enhanced chemiluminescence (Amersham) on autoradiography film (Kodak). Transfected cells were treated with doxorubicin (2 μmol/L) for 4 h and assayed for apoptosis by Annexin V-FITC staining (BD Pharmingen).

Immunofluorescent microscopy: Multiple myeloma cells ($1\times10^5$) were plated on double cytoslides (Shandon) by cytocentrifugation at 500 rpm for 3 min and fixed with 1% paraformaldehyde (Fisher Scientific) on ice for 30 min. Permeabilization of cells was done with 0.5% Triton X-100 (Sigma) in PBS at room temperature for 60 min. Cells were stained with a polyclonal antibody against topo IIα, which was produced in our laboratory [PAB454; Sullivan D M, et al., *Biochemistry* (1989)28; 5680-7]. The topo IIα antibody was diluted 1:100 in a buffer containing 1% bovine serum albumin (Sigma) and 0.1% Igepal CA-630 (Sigma) in PBS and incubated for 1 h at room temperature. After three washes with PBS, slides were incubated with a secondary anti-rabbit Alexa Fluor 594 (Invitrogen) in addition to a cytoskeletal protein stain, phalloidin-Alexa Fluor 488 conjugate (Invitrogen). Each was diluted 1:1,000 in 1% bovine serum albumin and 0.1% Igepal CA-630 in PBS and incubated for 40 min at room temperature. Slides were washed four times in PBS and once in distilled water, and the nuclei were stained with 4',6-diamidino-2-phenylindole (DAPI; Vector Laboratories). Immunofluorescence was observed with the Zeiss Axio Imager Z1 microscope (Carl Zeiss Microimaging) with an Axiocam MRm camera (Carl Zeiss Microimaging). Two experiments were done with 50 cells assayed per experiment. Cells were chosen randomly and scored as nuclear or cytoplasmic when ≥90% of the fluorescence was in the respective cellular compartment.

Band depletion assay: Band depletion assays were done as described by Xiao et al. and colleagues [Xiao H, et al., *Proc Natl Acad Sci USA* (2003)100:3239-44]. Briefly, $5\times10^5$ cells were lysed in 50 μL alkaline lysis solution for 30 min on ice (200 mmol/L NaOH, 2 mmol/L EDTA), and the lysate was neutralized by the addition of 4 μL of both 1 mol/L HCl and 1.2 mol/L Tris (pH 8.0). The lysate was then mixed with 30 μL of 3×SDS sample buffer [150 mmol/L Tris-HCl (pH 6.8), 6 mmol/L EDTA, 45% sucrose, 9% SDS, and 10% β-mercaptoethanol] and separated on 8% SDS-PAGE gels.

Comet assay: Log-density H929 myeloma cells were plated at a concentration of $2\times10^5$/mL, and plateau-density cells were plated at $2\times10^6$/mL. All cells were grown in 24-well plates (Falcon) with 1 mL sample/well. Drug treatment groups were vehicle only (1 μL/mL DMSO), 10 μmol/L VP-16, 5 nmol/L ratjadone C, or a combination of 10 μmol/L VP-16 and 5 nmol/L ratjadone C. Cells that were treated with ratjadone C were first plated at log or plateau density and incubated for 16 h with ratjadone C or vehicle, after which VP-16 was added for 1 h. After 1 h of VP-16 exposure, the comet assay was done as described by Kent et al. [Kent C R, et al., *Int J Radial Biol* (1995)67:655-60] and modified by Chen et al. [Chen Q, et al., *Blood* (2005)106:698-705]. To ensure random sampling, 50 images were captured per slide on a Leica fluorescent microscope and quantified with ImageQuant software (Molecular Dynamics). The average comet moment value obtained from vehicle control samples was subtracted from the average comet moment of each drug treatment sample. The data shown are mean±SD of two separate experiments.

Additional drug combinations in H929 human myeloma cell lines: H929 human myeloma cell lines were placed at high density ($4\times10^6$) with and without 5 nmol/L ratjadone C and incubated for 16 h. Cells were then incubated for 4 h with one of the following: 2 μmol/L doxorubicin, 10 μmol/L VP-16, 10 µmol/L melphalan, or 10 µmol/L Velcade. Cells were assayed for apoptosis by terminal deoxynucleotidyl transferase-mediated dUTP nick end labeling staining.

Results

Log- and plateau-density myeloma cells: The myeloma cell lines 8226, H929, and U266 were grown at log-density ($2\times10^5$ cells/mL) and plateau-density ($2\times10^6$ cells/mL) growth conditions for 16 h. Cells were then treated with the topo II inhibitor doxorubicin (2 µmol/L) for 4 h and assayed for apoptosis by activated caspase-3 expression. Cells grown at plateau densities and treated with 2 µmol/L doxorubicin were found to have extremely low levels of apoptosis compared with results shown for log-phase cells (FIG. 1A). Thus, this shows that cells grown at different densities exhibit specific characteristics, such as drug resistance and nuclear-cytoplasmic trafficking of topo IIα. The topo IIα isozyme, topo IIβ, is not exported from the nucleus in human myeloma cells [Valkov N I, et al., *Br J Haematol* (2000)108:331-45].

Intracellular trafficking of topo IIα: Cells grown at log and plateau densities and ratjadone C-treated cells (100 cells per experiment) were scored as "nuclear" or "cytoplasmic" if ≥90% of topo IIα was in that compartment as determined by fluorescence microscopy (FIG. 1B). For myeloma cells grown at log-phase concentrations, 73% to 87% of cells had ≥90% of the topo IIα in the nucleus; for cells grown at plateau-phase concentrations, 85% to 93% of cells had ≥90% of the topo IIα in the cytoplasm. CRM1 inhibition by ratjadone C was found to block export of topo IIα in cells grown in plateau-phase conditions (FIG. 1B).

Topo IIα trafficking and CRM1 inhibition: H929 human myeloma cells were grown at log and plateau densities and stained for cytoskeletal protein (phalloidin; green), topo IIα (red), and DNA (DAPI; blue). Results indicate that topo IIα was present in the nucleus of log-density cells and was exported from the nucleus in plateau-density cells (FIG. 2). Nuclear export was blocked in plateau cells by the CRM1 inhibitor ratjadone C and by transfection with a CRM1-specific siRNA. Under the conditions of this experiment, CRM1 siRNA knockdown was 69%. For ratjadone C-treated plateau-density cells (FIG. 1B), ~70% of the cells had ≥90% topo IIα in the nucleus for each myeloma cell line.

CRM1 inhibitor and topo IIα inhibitor synergy: The myeloma cell lines 8226, H929, and U266 were grown for 16 h at plateau densities in the presence of ratjadone C (5 nmol/L). The cells were then treated with doxorubicin (2 µmol/L) for 4 h and assayed for apoptosis by caspase-3 staining with the use of flow cytometry (n=3 for each cell line). FIG. 3A shows that myeloma cells were rendered more sensitive to the topo II inhibitor by inhibition of CRM1 export with ratjadone C. FIGS. 4A to 4C illustrate that high cell density-induced drug resistance is reversed by the CRM1 inhibitor ratjadone C. Ratjadone C is a potent inhibitor of CRM1 and prevents nuclear export by alkylating the active site $Cys^{528}$ amino acid residue of CRM1. Ratjadone C has reduced toxicity in vitro compared to leptomycin B when used at low concentrations [Falini B, et al., *Blood* 2006; 107:4514-23].

CRM1 inhibitor sensitizes patient myeloma cells to topo II drugs: Human bone marrow aspirates were obtained from multiple myeloma patients and purified by Ficoll-Paque gradient. Bone marrow samples with >75% plasma cells, as determined by toluidine blue staining and microscopy, were used for each assay (n=7). Cells were placed at plateau concentration ($4\times10^6$/mL), treated with ratjadone C (5 nmol/L) for 16 h followed by doxorubicin (2 µmol/L) for 4 h, and assayed for cleaved caspase-3 to determine apoptosis. Cells treated with ratjadone C were significantly (P=0.0003) more sensitive to doxorubicin (3-fold) than doxorubicin alone (FIG. 3B). Normal cells, including flow 2,000 cells and peripheral blood mononuclear cells (n=5), were not sensitized by the CRM1 inhibitor (P=0.22). FIG. 3B shows peripheral blood mononuclear cells only.

CRM1 inhibitor and topo IIα poisons: The human myeloma cell lines 8226, H929, and U266 were incubated at high density ($2\times10^6$ cells/mL) for 16 h in the presence of the CRM1 inhibitor ratjadone C (5 nmol/L). Cell cultures were then exposed to the topo II-targeted agents VP-16 (10 µmol/L) for 8 h or doxorubicin (2 µmol/L) for 4 h and assayed for apoptosis with a caspase-3 assay (BD Pharmingen). In addition, to show whether the ratjadone C/doxorubicin and the ratjadone C/VP-16 synergistic activities were because of topo IIα nuclear localization, cells were transfected with a siRNA to knockdown topo IIα expression (FIGS. 12 and 13). Topo IIα knockdown was >90% when assayed by Western blot (FIG. 3C, inset). In myeloma cell lines, with both topo II inhibitors (doxorubicin and VP-16), we found that knockdown of topo IIα protein expression reversed the synergistic effect and reduced apoptosis to untreated levels (4-12% apoptosis; FIG. 4C).

CRM1 siRNA sensitizes myeloma cells to topo IIα poisons: In addition to CRM1 pharmacologic modification by a chemical agent, a CRM1-specific siRNA was used to determine whether the observed synergistic activity could be reproduced in another model system. H929 cells were transfected by electroporation with a CRM1-specific siRNA (FIG. 9). After transfection, the cells were incubated at log-phase densities for 24 h to allow CRM1 siRNA-mediated knockdown and then concentrated at plateau-phase conditions for an additional 16 h. CRM1 knockdown cells grown at high density for 16 h were then treated with the topo II inhibitor doxorubicin (2 µmol/L) for 4 h and assayed for apoptosis by Annexin V staining using flow cytometry (FIG. 3). CRM1 knockdown was found to increase the effectiveness of doxorubicin. Myeloma cell line 8226 showed similar results (data not shown). To show efficient siRNA knockdown, SDS lysates of equal cell numbers were assayed for CRM1 by Western blot (FIG. 10).

Increase in cleavable complex formation by CRM1 inhibition: VP-16 stabilizes DNA-topo IIα adducts, resulting in double-stranded DNA breaks. One hypothesis is that, when topo IIα is kept in the nucleus by ratjadone C, a greater number of DNA-topo IIα complexes would be observed. To assay this potential effect, several band depletion assays were done (n=3). Band depletion assays can assess the amount of topo IIα-DNA covalent complexes formed in intact cells. Large covalent complexes will have decreased migration into a SDS-PAGE gel; therefore, the amount of topo IIα, as measured by Western blot, will be depleted. VP-16 alone did not produce significant band depletion; however, when used together with ratjadone C, a large depletion at both 25 and 50 µmol/L VP-16 concentrations was observed (FIG. 4A). These data indicate that blocking nuclear export of topo IIα will increase the effectiveness of VP-16 and induce apoptosis by increased cleavable complexes.

Comet assay: Plateau-density H929 cells were treated with 5 nmol/L ratjadone C for 16 h and then with 10 µmol/L VP-16 for 60 min. DNA fragmentation was measured by the neutral comet assay. The CRM1 inhibitor ratjadone C increased the DNA cleavage induced by the topo II inhibitor VP-16 (FIG. 4B). Increased DNA fragmentation led to increased apoptosis in cells treated with both VP-16 and ratjadone C.

Ratjadone C does not sensitize H929 human myeloma cell lines to other myeloma drugs: H929 myeloma cells were exposed to ratjadone C and various additional drug combinations (FIG. 5), including the alkylating agent melphalan and proteosome inhibitor Velcade. CRM1 inhibition sensitizes myeloma cells to the topo II inhibitors doxorubicin (P=0.00005) and VP-16 (P=0.02), but it did not significantly sensitizes myeloma cells treated with melphalan (P=0.35) or Velcade (P=0.30).

Example 2

Small Molecule Inhibitors of Nuclear Export of Topoisomerase IIα for the Treatment of Cancer Topo IIα is exported from the nucleus of human multiple myeloma (MM) cells by a CRM1-dependent mechanism [Engel et al, *Exp. Cell Res*. (2004)295(2):421-31]. Moreover, topo IIα has nuclear export signals (NES) at amino acids 1017-28 and 1054-66 [Turner et al, *J. Cell Sci*. (2004)117: 3061-71]. Drug resistance to topo II poisons occurs when topo II is trafficked to the cytoplasm where it is not in contact with the DNA, and thus unable to induce cell death. In addition, the inventors have shown above that blocking nuclear export with a CRM1 inhibitor or by siRNA sensitizes MM cells to topo II poisons.

In furtherance of the showing above in Example 1, the inventors have identified a group of 20 small molecule inhibitors (SMI) effective in the treatment of multiple myeloma (MM) and perhaps other cancers. In vitro data indicates that these drugs can be utilized as single agents or in combination with cancer drugs that target topoisomerase II alpha (topo IIα). Using computer-generated molecular modeling, the inventors have predicted 20 small molecules from the NCI database that bind to each of the two nuclear export signals of topo IIα and thereby improve the effectiveness of topo II-directed therapeutics.

Materials and methods: The structure of *S. cerevisiae* topo II was used to create a model of human topo IIα using the program PhyreA. The procedure for molecular docking involved selection of structural pockets at the NES in topo IIα suitable for interactions with drug-like small molecule inhibitors (SMI) and molecular docking simulations where 140,000 small molecules (mw<500) were analyzed. The 10/SMI/NES were tested by an in vitro assay for induction of apoptosis (caspase 3) and viability assays to determine the anti-proliferative activity using the CellTiter-Blue cell viability assay (Promega). Cell types used included human MM RPMI 8226 and NCI-H929 cells. SMI were tested both as single agents and in combination experiments with the topo II inhibitors doxorubicin and VP-16. In addition, immunofluorescence microscopy for the intracellular location of topo II in SMI treated MM cells was also performed.

Identified compounds: The top 10 scoring SMI for each of the two NES (20 total) were obtained from NCI and tested for cytotoxicity against human MM cells. Data from apoptosis assays indicate that several of the SMI sensitize MM cells when co-treated with doxorubicin. Robotic cell viability assays determined that several of the SMI had anti-proliferative activity. The IC50 values obtained from single drug cell viability assays revealed two SMI compounds with IC50 values of 4.7 and 11.1 μM. Drug combination assays demonstrated a synergistic effect with the topo IIα inhibitor doxorubicin. Immunofluoresence microscopy revealed an increase in topo II in the cell nucleus of cells treated for 24 hours with the lead SMI.

Figure 6:
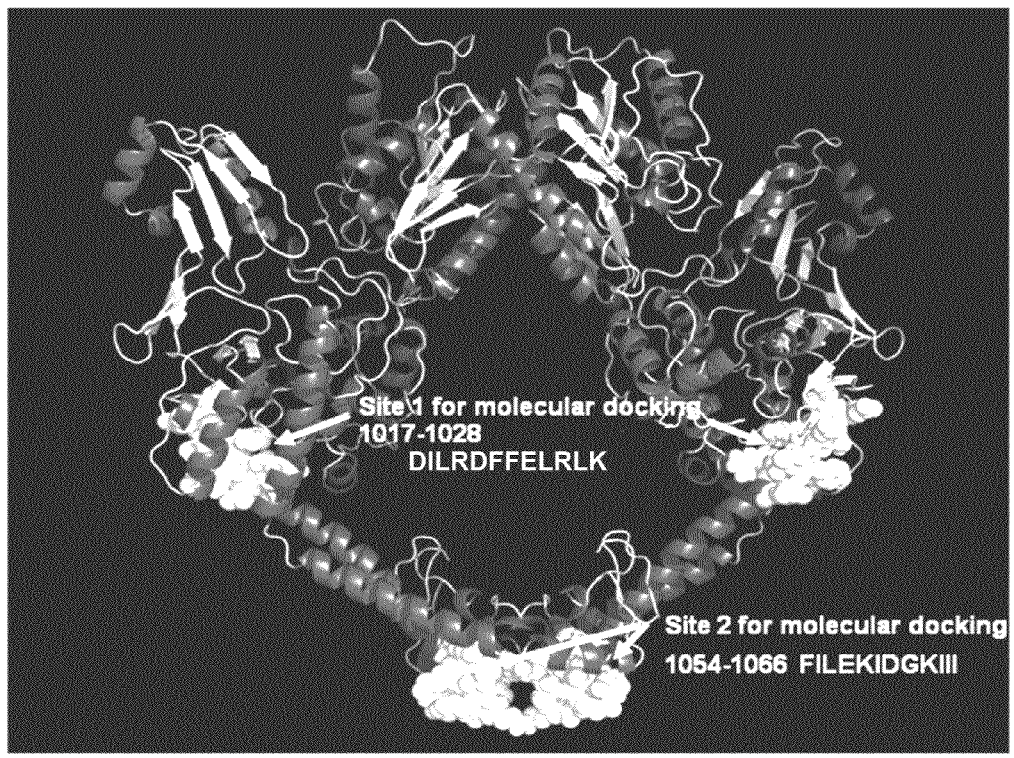
FIG. 6 shows the two nuclear export sequences, labeled sites 1 & 2 and appearing as white spheres, in the context of the native topoisomerase IIα homodimer. A first site is found at amino acids 1017-1028 comprising the sequence DILRDFFELRLK (SEQ ID NO: 1) and second site is found at amino acids 1054-1066 comprising the sequence FILE-KIDGKIII (SEQ ID NO: 2). The structure of *Saccharomyces cerevisiae* topo II was used to create a homology model of human topo IIα using the program PhyreA. A chemical ligand database containing approximately 140,000 small molecules (MW<500) was then molecularly docked onto the two nuclear export sites of human DNA topo IIα using DOCKv5.1.0. The procedure for molecular docking involved: 1) selection of structural pockets in DNA topo IIα suitable for interactions with drug-like small molecules, and 2) molecular docking simulations where each one of approximately 140,000 small molecules is positioned in the selected structural pocket. Ten small molecule inhibitors were predicted for each NES site.

The structure of *Saccharomyces cerevisiae* topo II, FIG. 6, was used to create a homology model of human topo IIα using the program PhyreA. A chemical ligand database containing approximately 140,000 small molecules (molecular weight<500) was then molecularly docked onto the two nuclear export sites of human DNA topo IIα using DOCKv5.1.0 with a previously described approach. The procedure for molecular docking involved: 1) selection of structural pockets in DNA topo IIα suitable for interactions with drug-like small molecules, and 2) molecular docking simulations where each one of approximately 140,000 small molecules (mw<500) is positioned in the selected structural pocket and scored based on predicted polar (e.g., H bond) and non-polar (e.g. van der Waals) interactions. The top 10 scoring compounds for nuclear export sites 1 and 2 were obtained from NCI and tested for cytotoxicity against human myeloma cancer cells. Preliminary data from apoptosis assays (below) indicate that several of the SMI may sensitize myeloma cells when co-treated with doxorubicin.

Optimization of the most active SMI will be initially done using the RACHEL ligand refinement software package, which combinatorially derivatizes a lead compound to improve ligand-receptor binding affinity within the nuclear export sequence target site in topo IIα. This strategy further provides the basis for future syntheses of highly selective inhibitors with a high affinity for nuclear export sequences in topo II.

Thus, using computer-generated molecular modeling, the inventors have identified 20 SMI (Table 1) from the NCI database that would bind to the two NES of topo IIα and thereby improve the effectiveness of topo II directed therapeutics, particularly in the treatment of MM. In vitro apoptosis assays indicate that these drugs may be effective as single agents or in combination with currently used cancer drugs that target topo II. These data have important clinical implications in the treatment of multiple myeloma.

Example 3

Blocking a Topo IIα Nuclear Export Signal Sensitizes Human Multiple Myeloma Cells to Topo IIα Inhibitors Topoisomerase IIα is exported from the nucleus of human multiple myeloma (MM) cells by a CRM1-dependent mechanism (Engel et al, Exp. Cell Res. 295(2):421-31, 2004). Nuclear export signals (NES) for topo IIα have been identified at amino acids 1017-28 (site 1) and 1054-66 (site 2) using mutated full-length FLAG-tagged topo IIα protein and immunofluorescence microscopy, (Turner et al, J. Cell Sci. 117:3061-71, 2004). Drug resistance to topo II poisons occurs when topo II is trafficked to the cytoplasm where it is not in contact with the DNA, and thus unable to induce cell death. In addition, blocking nuclear export with a CRM1 inhibitor or by siRNA sensitizes MM cells to topo II poisons, (Turner and Sullivan, Cancer Res. 69(17): 6899-6905, Sep. 1, 2009).

The structure of *S. cerevisiae* topo II was used to create a model of human topo IIα using the program PhyreA. The procedure for molecular docking involved selection of structural pockets at the NES in topo IIα suitable for interactions with drug-like small molecule inhibitors (SMI). Molecular docking simulations screened 140,000 small molecules (mw<500) from the NCI database. The top scoring SMI for each of the two NES (20 total) were obtained from NCI and tested for induction of apoptosis (caspase 3), and anti-proliferative activity using the CellTiter-Blue (Promega). Cell types used included human MM RPMI 8226 and NCI-H929 cells. SMI were tested both as single agents and in combination experiments with the topo II inhibitor doxorubicin. In addition, immunofluorescence microscopy for the intracellular location of topo IIα in SMI treated MM cells was also performed.

Low-density myeloma cells: Robotic cell viability assays determined that several of the SMI had anti-proliferative activity. However, only SMI that docked to NES site 1 showed any inhibition of viability. The IC50 values obtained from single drug cell viability assays in low density cells revealed two SMI compounds with IC50 values of 4.7 and 11.1 μM. None of the SMI affected the viability of high-density cells (IC50>100 μM).

High-density drug-resistant myeloma cells: Data from apoptosis assays indicate that four of the SMI that dock to NES site 1 do significantly (p<0.05) sensitize high density MM cells to doxorubicin. Immunofluorescence microscopy revealed an increase in topo IIα in the cell nucleus of cells treated for 20 hours with the four lead SMI.

Figure 7:
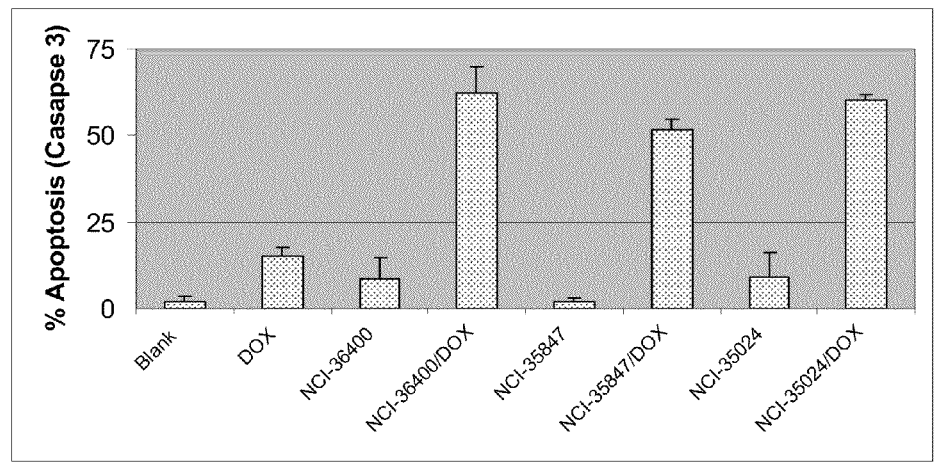
FIG. 7 is a graph showing that nuclear export signal ("NES") inhibitors synergize with doxorubicin to induce apoptosis. Log density cells (2e5/ml) were concentrated to plateau densities (2e6/ml) and treated with NES inhibitors NCI-36400, NCI-35847, NCI-35024 at 10 μM for 16 hours. These small molecule NES inhibitors dock at site 1. Cells were then exposed to 0.1% DMSO or 2 μM doxorubicin for 4 hours. Cells were assayed by flow cytometry for activated caspase 3 (n=4).
Figure 8:
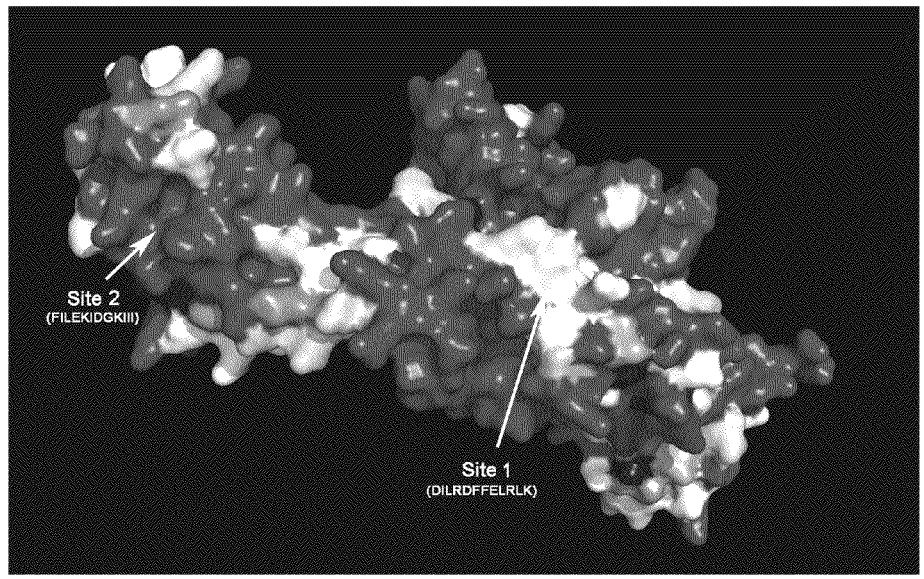
FIG. 8 is an illustration showing an atomic homology model of human topoisomerase IIα generated by the program Phyre. The molecular surface is colored based on sequence identity with yeast topo II calculated with clustalx and the Docker program (developed at UF). Red (dark gray in the gray-scale reproduction) represents 100% sequence identity, and colors are graded from red/orange (dark gray in the gray-scale reproduction—very little and indistinguishable from red)/yellow (white in the gray-scale reproduction)/green (light gray in the gray-scale reproduction) and blue (medium gray in the gray-scale reproduction) which would represent no sequence identity. Nuclear export sites 1 (A) and 2 (B)

Intracellular trafficking of topoisomerase IIα in log- and plateau-density myeloma cells resulted in differences in the ability of topo IIα inhibitors to induce apoptosis (FIG. 7). NCI-H929 (H929), RPMI 8226 (8226) and U226B1 (U226) human myeloma cells grown at plateau phase (high density) export topo IIα, whereas cells grown at log phase (low density) maintain topo IIα in the nucleus. Cells were grown for 16 hours at log or plateau densities and treated with 2 μM doxorubicin for 4 hours (n=2). Apoptosis was determined by caspase 3 staining with the use of flow cytometry (10,000 cells). As shown in FIG. 7, cells that maintained nuclear topo IIα were more sensitive to topo IIα-targeted chemotherapy.

Topo IIα is present in the nucleus of log density cells and is exported from the nucleus in plateau density cells, nuclear export is blocked by a CRM1 inhibitor (ratC) and CRM1 specific siRNA (FIG. 2). H929 human myeloma cells were grown at log and plateau densities, fixed with 4% paraformaldehyde, permeabalized with 0.25% Triton X-100, and stained for cytoskeletal protein (phalloidin-green when presented in color/light gray to white in the referenced gray-scale photo reproduction), topo IIα antibody (red when presented in color/gray in the referenced gray-scale photo reproduction), and the nucleus (DAPI-blue when presented in color/gray in the referenced gray-scale photo reproduction). Results indicate that CRM1 siRNA knockdown was 70% at 72 hours (FIG. 2).

CRM1 siRNA knockdown makes myeloma cells more sensitive to chemotherapy (FIG. 9). Cells were transfected with siRNA, incubated at log-phase for 24 hours, and concentrated at plateau-phase conditions. At 48 hours cells were treated with the topo II inhibitor doxorubicin (1 μM) and assayed for apoptosis by Anexin V staining using flow cytometry. Treatment of cells with CRM1 siRNA in combination with doxorubicin resulted in significantly greater apoptosis over treatment with CRM1 siRNA alone of Scram in combination with doxorubicin. FIG. 10 presents results of a Western blot for siRNA transfection, showing that CRM1 knockdown makes plateau density cells more sensitive to topoisomerase inhibitors.

Thus, using computer-generated molecular modeling, four lead compounds from the NCI database have been identified that bind to the site 1 NES of topo IIα. These lead compounds are SMI that synergize with the topo II inhibitor doxorubicin. In vitro apoptosis assays indicate that these drugs would be effective as single agents or in combination with cancer drugs that target topo II. These data have important clinical implications in the treatment of multiple myeloma.

TABLE 1

A1:[1] 3,6-diphenyl-1,2,4,5-tetraazinane (ACD/Name 4.0); C14H16N4; 240.3072; NCI 114057

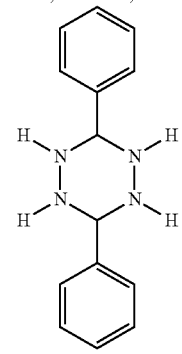

A3: 1-(2-naphthyl)-2-(15,3,5,7-tetraazatricyclo[3.3.1.1~3,7~]dec-1-yl)ethanone (ACD/Name 4.0); C18H21N4O 309.3901; NCI 36400

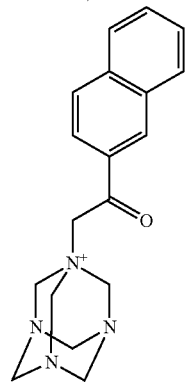

A4: 2,3,6,7,10,11-hexahydrotriimidazo[1,2-a: 1,2-c: 1,2-e][1,3,5]triazine (ACD/Name 4.0) C9H12N6 204.234 NCI 53040

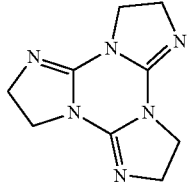 [SMILES: C1CN2C(=N1)N1CCN=C1N1CCN=C21]

A5: 1,4,7-tris(methoxymethyl)dodecahydro-1,4,7,9b-tetraazaphenalene (ACD/Name 4.0); C15H30N4O3; 314.427; NCI 82001

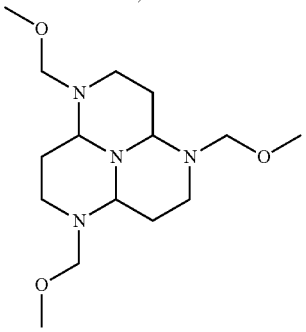

TABLE 1-continued

A6: 2,5,8-trimethyldodecahydro-1,4,7,9b-tetraazaphenalene
(ACD/Name 4.0); C12H24N4;
224.3484; NCI 218332

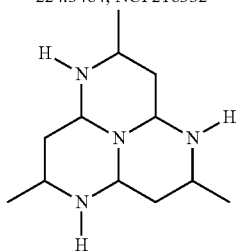

A8: N1,N4-bis(4-(4,5-dihydro-1H-imidazol-2-yl)phenyl)-2
(hydroxy(oxido)amino)terephthalamide
(ACD/Name 4.0); C26H23N7O4;
497.5122; NCI 35847

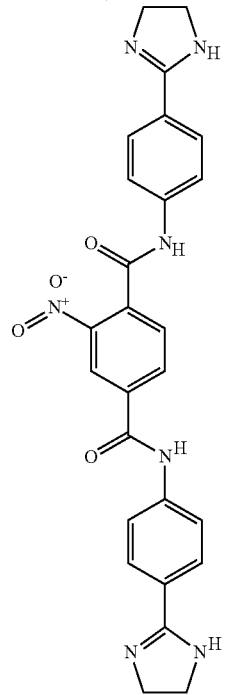

A9: ethyl 3-((2-chloro-5-(hydroxy(oxido)amino)-
6-methylhexahydro-4-pyrimidinyl)
amino)propanoate (ACD/Name 4.0);
C10H19ClN4O4; 294.7375; NCI 134514

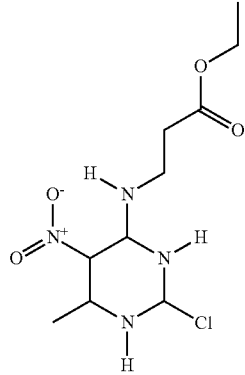 [SMILES: CCOC(=O)CCNC1NC(Cl)NC(C)C1[N+](=O)[O-]]

TABLE 1-continued

A10: 2-(15,3,5,7-tetraazatricyclo[3.3.1.1~3,7~]dec-1-yl)-
1-(5,6,7,8-tetrahydro-2-
naphthalenyl)ethanone (ACD/Name 4.0);
C18H25N4O; 313.4217; NCI 36791

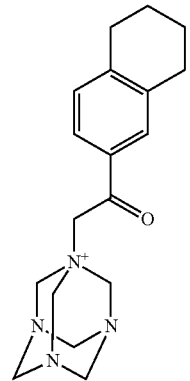 [SMILES: O=C(C[N+]12CN3CN(CN(C3)C1)C2)c1ccc2c(c1)CCCC2]

A12: 1-(4-iodophenyl)-2-(15,3,5,7-tetraazatricyclo
[3.3.1.1~3,7~]dec-1-yl)
ethanoneoxime (ACD/Name 4.0)
C14H19IN5O; 400.2415; NCI 35024

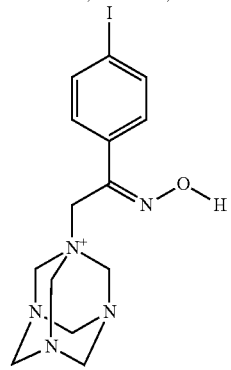

A14: methyl 4-(15,3,5,7-tetraazatricyclo[3.3.1.1~3,7~]
dec-1-ylmethyl)
phenyl sulfone (ACD/Name 4.0)
C14H21N4O2S; 309.4055; NCI 371729

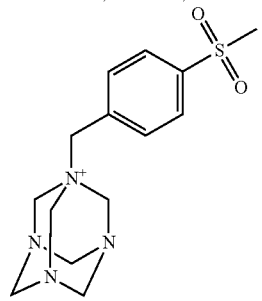

B1: Ethane-1,2-diphosphonic acid, C2H8O6P2,
MW190.0291 NCI 40837

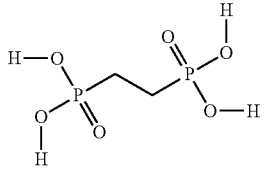

TABLE 1-continued

B2: (No Name); C6H8O6P2; 238.0731; NCI 608071

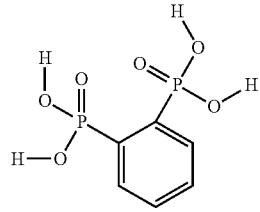 [SMILES: O=P(O)(O)c1ccccc1P(=O)(O)O]

B3: (bis(phosphonomethyl)amino)acetic acid
(ACD/Name 4.0); C4H11NO8P2;
263.0803; NCI 18468

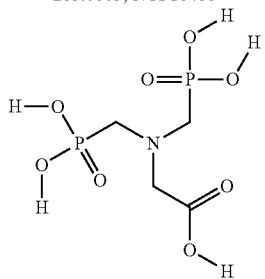

B4: 2,5-anhydro-3,4-dicarboxy-3,4-dideoxyhexaric acid
(ACD/Name 4.0); C8H8O9;
248.1458; NCI 122277

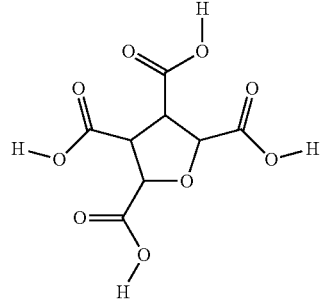 [SMILES: O=C(O)C1OC(C(=O)O)C(C(=O)O)C1C(=O)O]

B5: 5-hydroxy-1,2,3-benzenetricarboxylic acid
(ACD/Name 4.0); C9H6O7; 226.1422;
NCI 36997

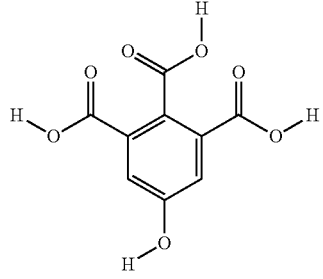 [SMILES: O=C(O)c1cc(O)cc(C(=O)O)c1C(=O)O]

B6: (3-(2-(1-naphthyl)ethyl)-2,4,5-trioxocyclopentyl)
(oxo)acetic acid (ACD/Name 4.0);
C19H14O6; 338.316; NCI 159456

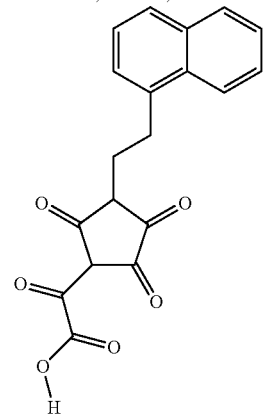

B7: 2-(hydroxy(oxido)amino)-3-phosphonobenzoic
acid (ACD/Name 4.0);
C7H6NO7P; 247.1007; NCI 129466

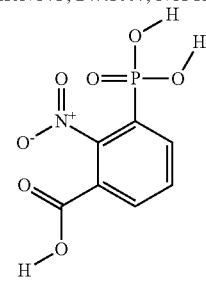

B8: 2,6-dioxo-1,3,5,7-adamantanetetracarboxylic acid
(ACD/Name 4.0); C14H12O10;
340.2428; NCI 117489

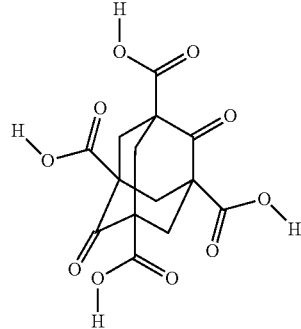 [SMILES: O=C(O)C12CC3(C(=O)O)CC(C(=O)O)(CC(C(=O)O)(C1)C3=O)C2=O]

TABLE 1-continued

B9: (No Name); C4H12O6P2; 218.0827; NCI 407819

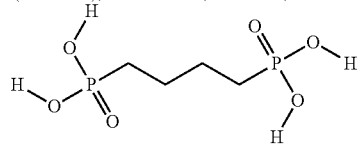

[1] Compound designations beginning with "A" refer to compounds that bind to site A, or site 1, of topoisomerase IIα. Similarly, compound designations beginning with "B" (see below) refer to compounds that bind to site B, or site 2, of topoisomerase IIα.

TABLE 2

A3: 1-(2-naphthyl)-2-(15,3,5,7-tetraazatricyclo[3.3.1.1~3,7~]dec-1-yl)ethanone

Docking score −52.108
MW 309.39
NCI 36400

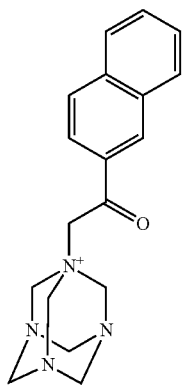 [SMILES: O=C(C[N+]12CN3CN(CN(C3)C1)C2)c1ccc2ccccc2c1]

A8: Terephthalanilide, 4',4''-di-2-imidazolin-2-yl-2-nitro-, hydrochloride

Docking score −50.122
MW 497.51
NCI 35847

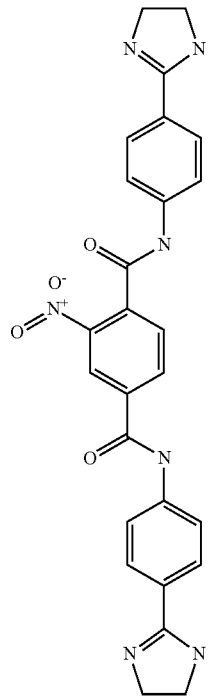

A12: 1-(4-iodophenyl)-2-(15,3,5,7-tetraazatricyclo [3.3.1.1~3,7~]dec-1-yl)ethanone oxime

TABLE 2-continued

Docking score −49.3289
MW 400.24
NCI 35024

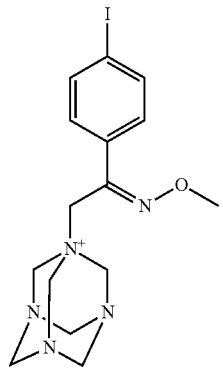 [SMILES: CO/N=C(/C[N+]12CN3CN(CN(C3)C1)C2)c1ccc(I)cc1]

All references cited in the present application are incorporated in their entirety herein by reference to the extent not inconsistent herewith.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

---

---

What is claimed is:

1. A method of treating multiple myeloma in a patient comprising administering to the patient in need thereof an effective amount of a combination of a compound that binds a nuclear export signal (NES inhibitor) on topoisomerase IIα and a topoisomerase inhibitor wherein the compound that binds the nuclear export signal is a small molecule inhibitor of nuclear export that binds to site 1 of the topoisomerase IIα molecule.

2. The method according to claim 1, wherein the small molecule is selected from the group consisting of:

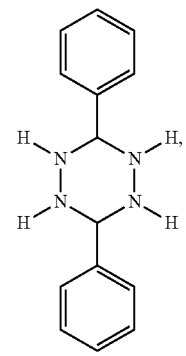

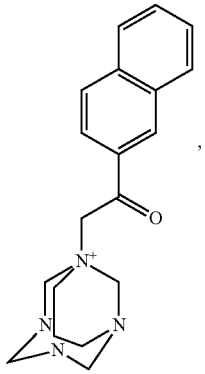

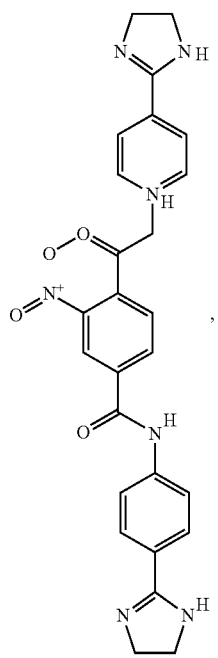

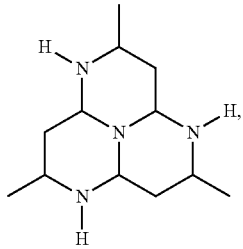

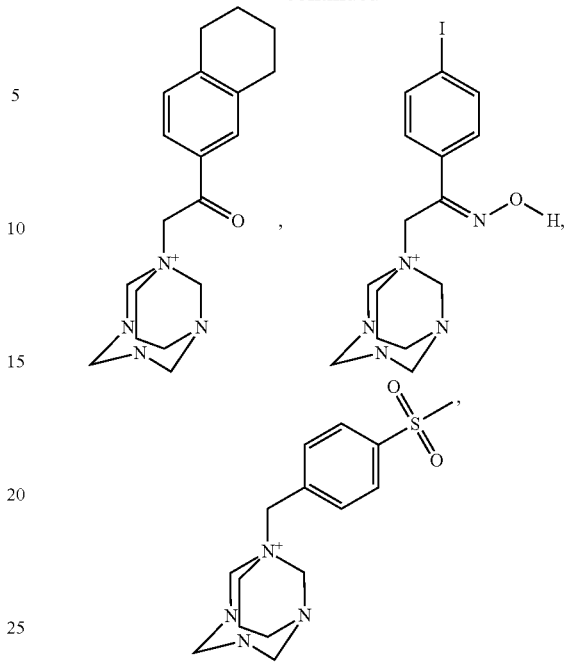

and combinations thereof.

3. The method according to claim 1 wherein the topoisomerase inhibitor is selected from the group consisting of doxorubicin, etoposide, etoposide phosphate, teniposide, epirubicin, daunomycin, amscrine and mitoxantrone.

4. The method according to claim 1 further comprising:
obtaining a sample from the patient; and
screening the sample for presence of cytoplasmic topo II α, wherein the patient is treated with an NES inhibitor responsive to detection of cytoplasmic topo II α.

5. A method of treating multiple myeloma in a patient comprising administering to the patient in need thereof an effective amount of a combination of a compound that binds a nuclear export signal on topoisomerase IIα and a topoisomerase inhibitor wherein the compound that binds the nuclear export signal is a small molecule inhibitor of nuclear export that binds to site 1 of the topoisomerase IIα molecule wherein the small molecule inhibitor is selected from the group consisting of:

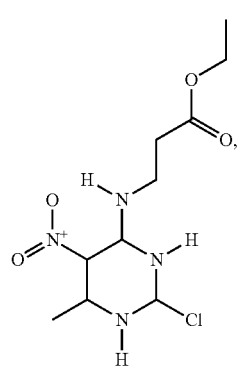

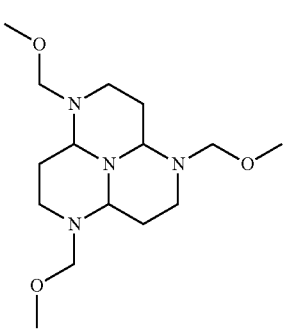

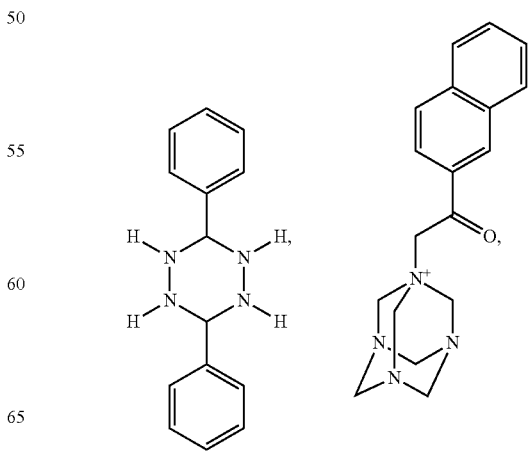

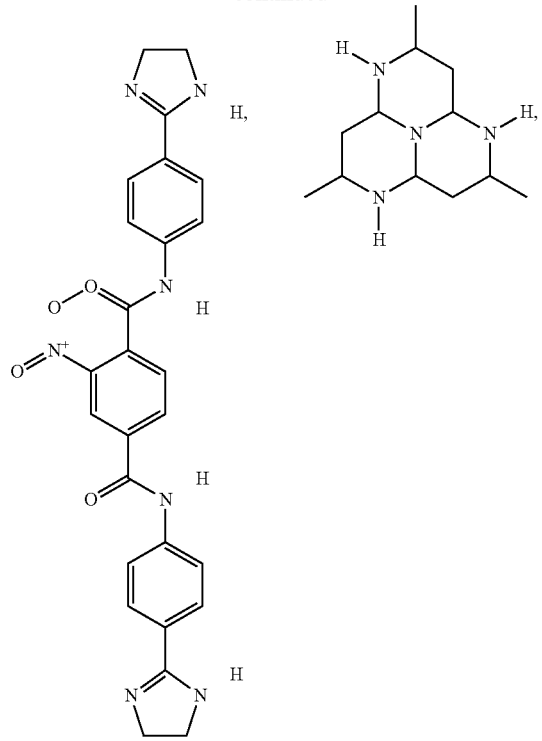

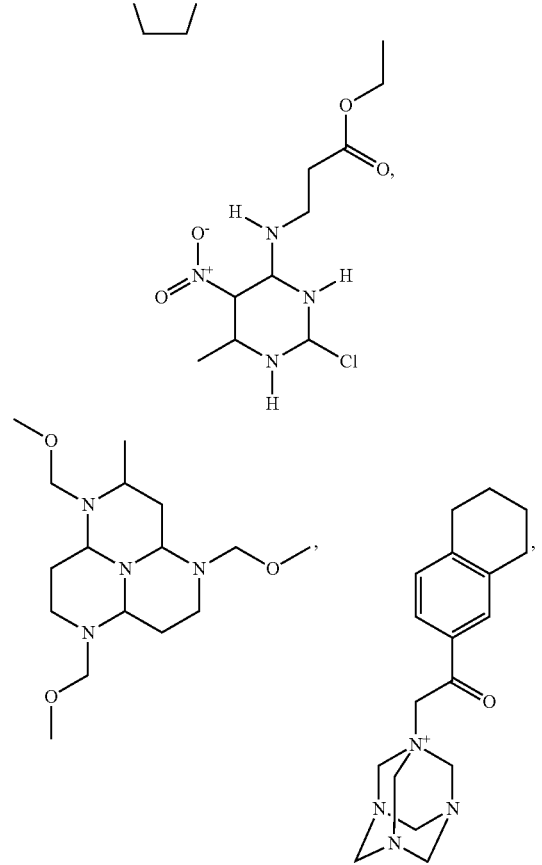

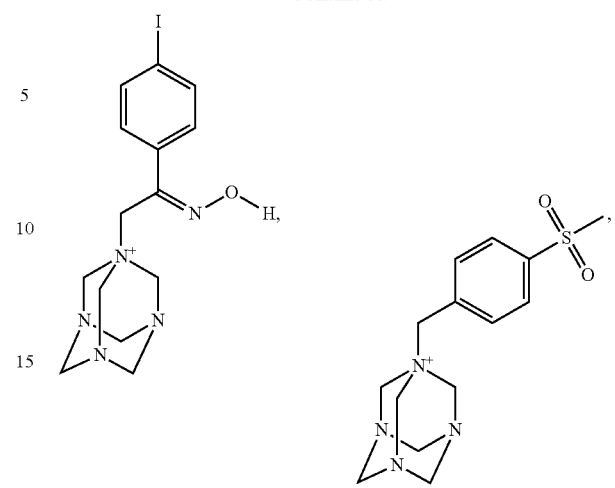

and combinations thereof.

6. The method according to claim 5 wherein the topoisomerase inhibitor is selected from the group consisting of doxorubicin, etoposide, etoposide phosphate, teniposide, epirubicin, daunomycin, amscrine and mitoxantrone.

7. A method of treating multiple myeloma in a subject comprising the step of administering to the subject in need thereof an effective amount of a topoisomerase inhibitor and a small molecule inhibitor of nuclear export that binds to site 1 of the topoisomerase IIα molecule wherein the small molecule inhibitor is

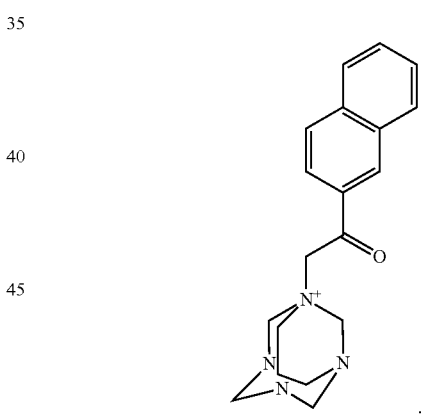

8. The method according to claim 7 wherein the topoisomerase inhibitor is selected from the group consisting of doxorubicin, etoposide, etoposide phosphate, teniposide, epirubicin, daunomycin, amscrine and mitoxantrone.

* * * * *